(12) United States Patent
Smith et al.

(10) Patent No.: US 7,988,318 B1
(45) Date of Patent: *Aug. 2, 2011

(54) APPARATUS AND METHOD FOR ILLUMINATING BLOOD

(75) Inventors: Kenneth L. Smith, Porum, OK (US); Mark D. Hose, Huntsville, AL (US)

(73) Assignee: Primos, Inc., Flora, MS (US)

( * ) Notice: Subject to any disclaimer, the term of this patent is extended or adjusted under 35 U.S.C. 154(b) by 336 days.

This patent is subject to a terminal disclaimer.

(21) Appl. No.: 12/197,092

(22) Filed: Aug. 22, 2008

Related U.S. Application Data

(63) Continuation-in-part of application No. 11/679,099, filed on Feb. 26, 2007, now Pat. No. 7,682,037.

(60) Provisional application No. 60/776,456, filed on Feb. 24, 2006.

(51) Int. Cl.
  *F21L 4/02* (2006.01)
  *F21V 33/00* (2006.01)
  *F21V 9/00* (2006.01)

(52) U.S. Cl. .................. 362/187; 362/184; 362/231

(58) Field of Classification Search ............ 362/184, 362/187, 230, 231, 477
See application file for complete search history.

(56) References Cited

U.S. PATENT DOCUMENTS

| | | | |
|---|---|---|---|
| 1,613,203 A * | 1/1927 | Shannon | 340/321 |
| 1,946,059 A * | 2/1934 | Buchholz | 362/184 |
| 4,725,460 A | 2/1988 | Matsuo et al. | |
| 4,804,850 A | 2/1989 | Norrish et al. | |
| 5,363,152 A | 11/1994 | Reed, III | |
| 6,250,771 B1 | 6/2001 | Sharrah et al. | |
| 6,290,368 B1 * | 9/2001 | Lehrer | 362/187 |
| 6,334,680 B1 | 1/2002 | Larson | |
| 6,485,160 B1 * | 11/2002 | Sommers et al. | 362/184 |
| 6,862,093 B2 | 3/2005 | Peng et al. | |
| 7,066,622 B2 | 6/2006 | Alessio | |
| 7,172,312 B2 | 2/2007 | Chen | |

(Continued)

OTHER PUBLICATIONS

Information about Related Patents and Patent Applications, see the section of the accompanying Information Disclosure Statement Letter entitled "Related Patents and Patent Applications" for further information.

(Continued)

*Primary Examiner* — David R Crowe
(74) *Attorney, Agent, or Firm* — Holland & Hart

(57) ABSTRACT

An apparatus including a light-emitting device configured to illuminate blood is described. The light-emitting device may include a red light source configured to emit red light. The light-emitting device may also include a green light source configured to emit green light. The light-emitting device may additionally include a first refractive lens and a reflector having a concave surface to reflect a portion of red light emitted by the red light source and a portion of green light emitted by the green light source toward the first refractive lens. The first refractive lens may be configured to direct red light emitted by the red light source to form a red light beam and to direct green light emitted by the green light source to form a green light beam. Additionally, the light-emitting device may include an optical adjuster configured to adjust a separation distance between the first refractive lens and at least one of the green light source and the red light source. The optical adjuster may further be configured to move the first refractive lens with respect to at least one of the red light source and the green light source. A method for illuminating blood is additionally disclosed.

19 Claims, 29 Drawing Sheets

U.S. PATENT DOCUMENTS

| | | |
|---|---|---|
| 7,290,896 B2 | 11/2007 | Dallas et al. |
| 7,699,482 B2 | 4/2010 | Noguchi |
| 2003/0227774 A1* | 12/2003 | Martin et al. ............... 362/240 |
| 2004/0200980 A1 | 10/2004 | Blackwell et al. |
| 2004/0223342 A1* | 11/2004 | Klipstein et al. ............. 362/555 |
| 2005/0185403 A1* | 8/2005 | Diehl ............................ 362/259 |
| 2007/0086186 A1* | 4/2007 | Rohlfing et al. ............. 362/240 |
| 2007/0153512 A1 | 7/2007 | Hendrie |
| 2007/0195420 A1 | 8/2007 | Fitchmun |
| 2008/0158875 A1* | 7/2008 | Kim et al. ..................... 362/231 |

OTHER PUBLICATIONS

Coolflashlights.com. "Hunting LED flashlights", archived Feb. 20, 2006, available http://web.archive.org/web/20060220151 19/http://www.coolflashlights.com/hunting_lights.html (3 of 3) Jul. 21, 2008 3:42:12 PM.

Internet advertisement for Risk Reactor's B40LEDBT—CAM Blacklite Flashlight; date unknown.

Internet advertisement for Xenopus Electronix Blood Tracking Light; date unknown.

Internet advertisement for Xenopus Electronix BloodTracker 40-LED Blood Tracking Flashlight; date unknown.

Advertisement on Ebay for Winchester Blood Trail Tracking L.E.D. Flashlight; Apr. 18, 2007.

\* cited by examiner

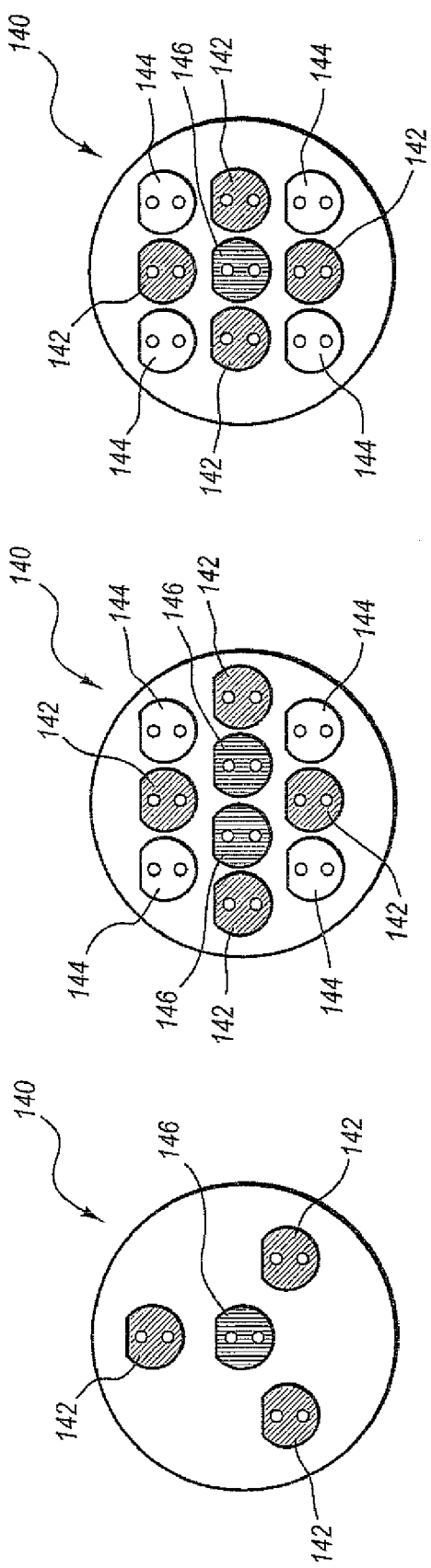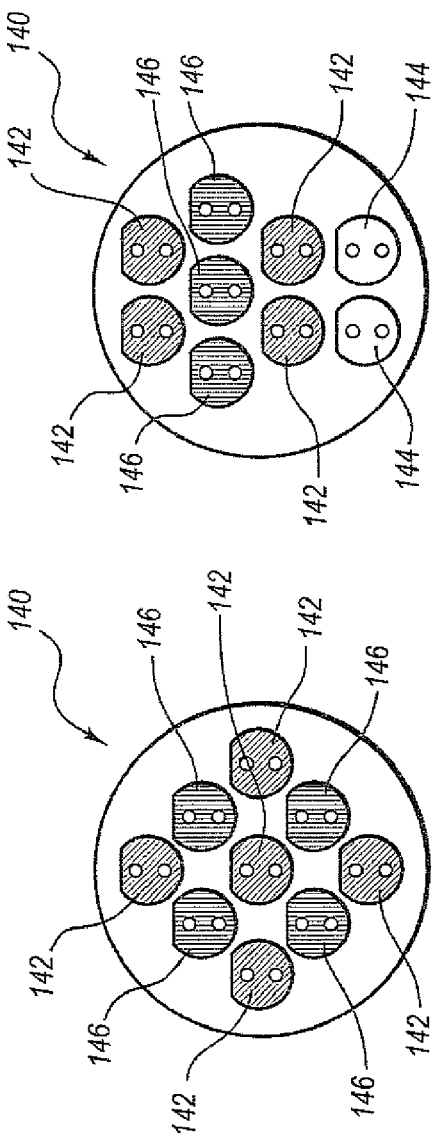

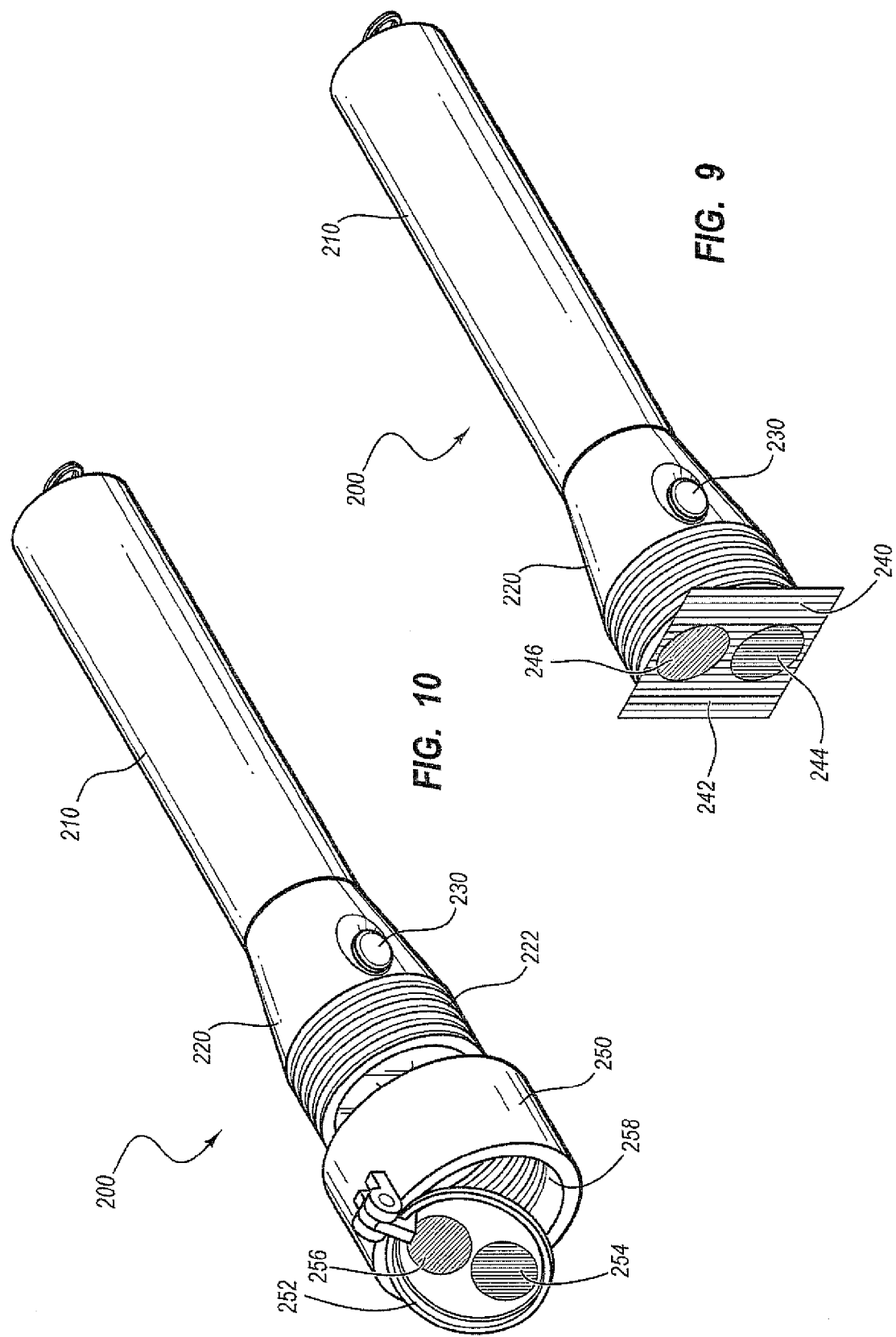

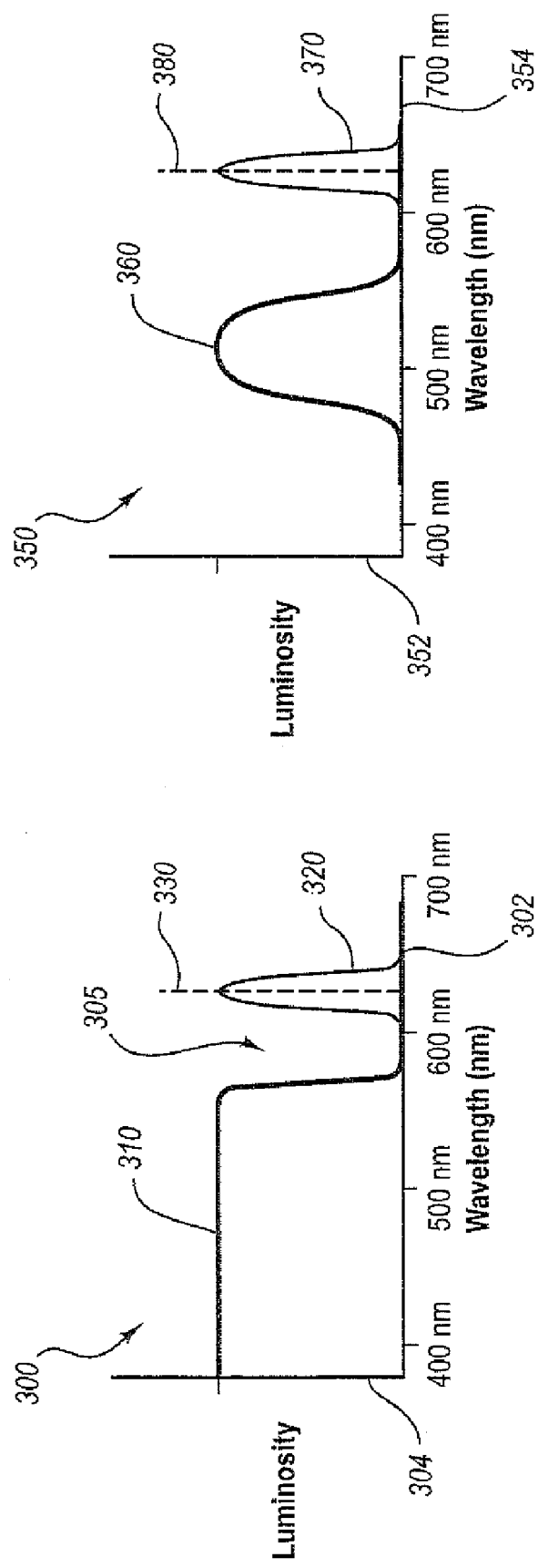

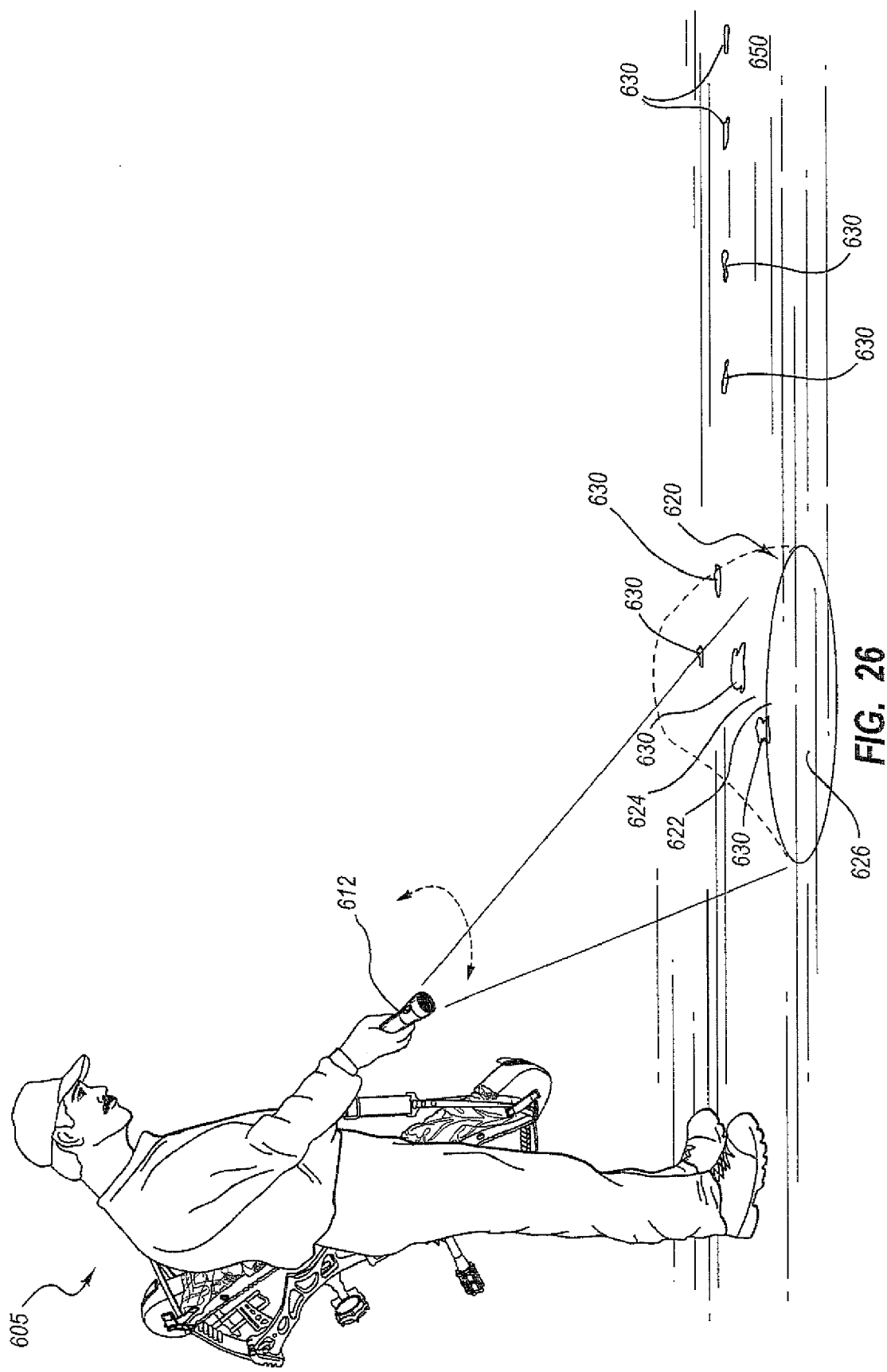

APPARATUS AND METHOD FOR ILLUMINATING BLOOD

CROSS REFERENCE TO RELATED APPLICATION

This application is a Continuation-in-Part of U.S. application Ser. No. 11/679,099, filed 26 Feb. 2007, the disclosure of which is incorporated, in its entirety, by this reference. Application Ser. No. 11/679,099, and likewise this application, claims the benefit of U.S. Provisional Application No. 60/776,456, filed 24 Feb. 2006, the disclosure of which is incorporated in its entirety by this reference.

BACKGROUND

Hunters often try to track wounded game by following a blood trail. Law enforcement officers and military personnel may also need to track a trail of blood. Following a blood trail at night may be challenging because blood is often difficult to identify at night, even if the tracker is using a high-powered flashlight. One problem with traditional flashlights is that they may flood a user's eye with a broad spectrum of light, making it difficult for the user to distinguish between the color(s) of blood and other colors. What is needed, therefore, is a device capable of generating a light spectrum that may helping hunters and others identify blood.

SUMMARY

In certain embodiments, an apparatus may comprise a light-emitting device for illuminating blood. The light-emitting device may comprise a green light source configured to emit green light. The light-emitting device may also comprise a red light source configured to emit red light. The green and red light sources may be configured such that at least a portion of the green light and at least a portion of the red light combine to form a combined light area. The combined light area may cause a red color to be perceived as standing out in contrast to non-red colors.

In at least one embodiment, the light-emitting device may comprise electronics adapted to modulate the red light. According to some embodiments, the green light source may comprise a first green light-emitting diode and the red light source may comprise a first red light-emitting diode. The light-emitting device may also comprise a lens placed over the first green and red light-emitting diodes. At least a portion of the lens may comprise a diffuser that allows more green light than red light to pass through.

According to various embodiments, at least one of the first red and green light-emitting diodes may comprise an output rating of at least three watts. In some embodiments, the light-emitting device may comprise a first reflective surface dimensioned to direct the red light and a second reflective surface dimensioned to direct the green light. In at least one embodiment, the light-emitting device may comprise a second red light-emitting diode, a second green light-emitting diode, and a third green light-emitting diode. The second red light-emitting diode may be positioned at least partially between the second and third green light-emitting diodes.

According to some embodiments, the red light may comprise a peak wavelength between approximately 630 nanometers and approximately 680 nanometers, and the green light may comprise a peak wavelength between approximately 500 nanometers and approximately 540 nanometers. In at least one embodiment, the red light may comprise a peak wavelength of approximately 660 nanometers. The green and red light sources may be configured such that the combined light area causes a blood-red color to be perceived as standing out in contrast to other colors. The red light source may comprise a bandwidth of less than 30 nanometers. According to various embodiments, the light-emitting device may comprise a flashlight. In certain embodiments, the light-emitting device may comprise a micro-controller programmable to adjust the intensity of at least one of the red or green light sources.

In certain embodiments, an apparatus may comprise a flashlight adaptor for illuminating blood. The flashlight adaptor may comprise a green filter configured to transmit green light. The flashlight adaptor may also comprise a red filter configured to transmit red light. The green and red filters may be configured such that at least a portion of the green light and at least a portion of the red light combine to form a combined light area. The combined light area may cause a red color to be perceived as standing out in contrast to non-red colors. The apparatus may also comprise a filter housing configured to attach the green and red filters to a flashlight.

According to various embodiments, a lens may comprise the green and red filters. In at least one embodiment, the red light may comprise a peak wavelength between approximately 630 nanometers and approximately 680 nanometers, and the green light may comprise a peak wavelength between approximately 500 nanometers and approximately 540 nanometers. According to certain embodiments, the red light may comprise a peak wavelength of approximately 660 nanometers. In various embodiments, the green and red light filters may be configured such that the combined light area causes a blood-red color to be perceived as standing out in contrast to other colors. The red light may comprise a bandwidth of less than 30 nanometers.

In certain embodiments, an apparatus may comprise a flashlight adaptor for illuminating blood. The flashlight adaptor may comprise a green filter configured to transmit green light and a red light source configured to emit red light. The green filter and the red light source may be configured such that at least a portion of the green light and at least a portion of the red light combine to form a combined light area. The combined light area may cause a red color to be perceived as standing out in contrast to non-red colors. The apparatus may also comprise a filter housing configured to attach the green filter and the red light source to a flashlight.

According to at least one embodiment, the light-emitting flashlight adaptor may be configured to modulate the red light. In some embodiments, the red light may comprise a peak wavelength between approximately 630 nanometers and approximately 680 nanometers, and the green light may comprise a peak wavelength between approximately 500 nanometers and approximately 540 nanometers. According to certain embodiments, the red light may comprise a peak wavelength of approximately 670 nanometers. In various embodiments, the green and red light filters may be configured such that the combined light area causes a blood-red color to be perceived as standing out in contrast to other colors. In some embodiments, the green filter may comprise etched glass.

A method may comprise providing a light-emitting device and including a green light source in the light-emitting device. The green light source may be configured to emit green light. The method may also comprise including a red light source in the light-emitting device. The red light source may be configured to emit red light. The green and red light sources may be configured such that at least a portion of the green light and at least a portion of the red light may combine to form a combined light area. The combined light area may cause a red color to be perceived as standing out in contrast to non-red colors.

In at least one embodiment, the method may comprise emitting the green light, emitting the red light, and combining the green light and the red light. In certain embodiments, the method may also comprise modulating the red light. In at least one embodiment, the red light may comprise a peak wavelength between approximately 630 nanometers and approximately 680 nanometers, and the green light may comprise a peak wavelength between approximately 500 nanometers and approximately 540 nanometers. According to certain embodiments, the red light may comprise a peak wavelength of approximately 670 nanometers. In various embodiments, the green and red light filters may be configured such that the combined light area causes a blood-red color to be perceived as standing out in contrast to other colors.

An apparatus may comprise a light-emitting device for illuminating blood. The light-emitting device may comprise a green light source configured to emit green light having a peak wavelength between approximately 500 nanometers and approximately 540 nanometers. The light-emitting device may also comprise a red light source configured to emit red light having a peak wavelength between approximately 630 nanometers and approximately 680 nanometers. The green and red light sources may be configured such that at least a portion of the green light and at least a portion of the red light combine to form a combined light area. The combined light area may cause a blood-red color to be perceived as standing out in contrast to other colors According to at least one embodiment, an apparatus may comprise a light-emitting device configured to illuminate blood, the light-emitting device including a red light source configured to emit red light and a green light source configured to emit green light. The light-emitting device may also comprise a first refractive lens configured to direct red light emitted by the red light source to form a red light beam and to direct green light emitted by the green light source to form a green light beam. The red light source and the green light source may be configured such that the red light beam and the green light beam are substantially non-overlapping. Additionally, the light-emitting device may comprise an optical adjuster configured to adjust a separation distance between the first refractive lens and at least one of the red light source and the green light source.

According to certain embodiments, an apparatus may comprise a light-emitting device configured to illuminate blood, the light-emitting device comprising a red light source configured to emit red light and a green light source configured to emit green light. The light-emitting device may also comprise a first refractive lens and a reflector having a concave surface to reflect a portion of red light emitted by the red light source and a portion of green light emitted by the green light source toward the first refractive lens. The first refractive lens may be configured to direct red light emitted by the red light source to form a red light beam and to direct green light emitted by the green light source to form a green light beam. The red light source and the green light source may be configured such that the red light beam and the green light beam are substantially non-overlapping.

According to additional embodiments, an apparatus may comprise a light-emitting device configured to illuminate blood, the light-emitting device comprising a first light source configured to emit red light and a second light source configured to emit visible light having a peak wavelength of approximately 565 nanometers or less. The light-emitting device may additionally comprise a refractive lens and a reflector having a concave surface to reflect a portion of red light emitted by the first light source and a portion of visible light emitted by the second light source toward the refractive lens. The refractive lens may be configured to direct red light emitted by the first light source to form a first light beam and to direct visible light emitted by the second light source to form a second light beam. The first light source and the second light source may be configured such that the first light beam and the second light beam are substantially non-overlapping.

According to various embodiments, an apparatus may comprise a light-emitting device configured to illuminate blood, the light-emitting device comprising a first light source configured to emit a first light beam comprising red light and a second light source configured to emit a second light beam comprising visible light having a peak wavelength of approximately 565 nanometers or less. The first light source and the second light source may be configured such that the first light beam and the second light beam are adjacent along their lengths and substantially non-overlapping.

According to at least one embodiment, a method of illuminating blood may comprise providing a light-emitting device configured to illuminate blood, the light-emitting device comprising a first light source configured to emit red light and a second light source configured to emit visible light having a peak wavelength of approximately 565 nanometers or less. The light-emitting device may also comprise a refractive lens configured to direct red light emitted by the first light source to form a first light beam and to direct visible light emitted by the second light source to form a second light beam. The first light source and the second light source may be configured such that the first light beam and the second light beam are substantially non-overlapping. The method may additionally comprise emitting red light from the first light source and visible light from the second light source to form the first light beam and the second light beam. The method may further comprise moving the light-emitting device such that the first light beam and the second light beam alternately illuminate a target location, causing a red color in the target location to be perceived as standing out in contrast to non-red colors.

BRIEF DESCRIPTION OF THE DRAWINGS

The accompanying drawings illustrate a number of exemplary embodiments and are part of the specification. Together with the following description these drawings demonstrate and explain various principles of the instant disclosure.

FIG. 3 is a front view of an exemplary light source according to certain embodiments.

FIG. 4 is a front view of an exemplary light source according to certain embodiments.

FIG. 5 is a front view of an exemplary light source according to certain embodiments.

FIG. 6 is a front view of an exemplary light source according to certain embodiments.

FIG. 7 is a front view of an exemplary light source according to certain embodiments.

FIG. 9 is a perspective view of an exemplary light-emitting device with a filter according to certain embodiments.

FIG. 10 is a perspective view of the exemplary light-emitting device illustrated in FIG. 9 according to certain embodiments.

FIG. 13 is a graph of relative sensitivity and wavelength of an exemplary light-emitting device according to certain embodiments.

FIG. 14 is a graph of relative sensitivity and wavelength of an exemplary light-emitting device according to certain embodiments.

FIG. 26 is a scene illustrating an exemplary use of a light-emitting device according to certain embodiments.

DETAILED DESCRIPTION OF EXEMPLARY EMBODIMENTS

Figure 2:
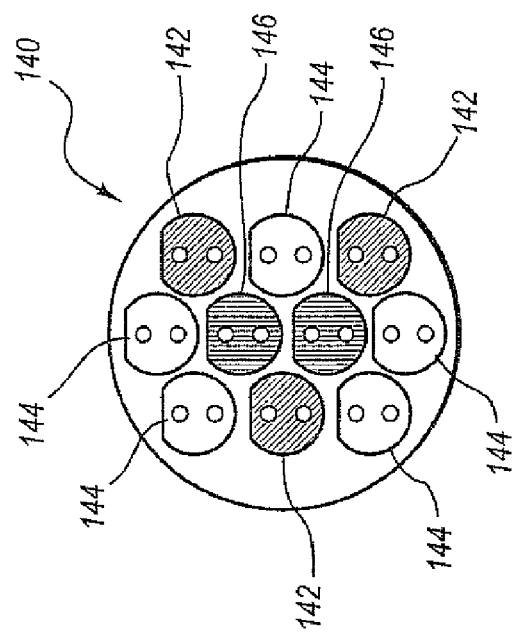
FIG. 2 is a front view of an exemplary light source of the light-emitting device illustrated in FIG. 1 according to certain embodiments.

Throughout the drawings, identical reference characters and descriptions indicate similar, but not necessarily identical, elements. While embodiments of the instant disclosure are susceptible to various modifications and alternative forms, specific embodiments have been shown by way of example in the drawings and will be described in detail herein. However, one of skill in the art will understand that embodiments of the instant disclosure are not intended to be limited to the particular forms disclosed herein. Rather, the instant disclosure covers all modifications, equivalents, and alternatives falling within the scope of embodiments defined by the appended claims.

The light-emitting devices presented in the instant disclosure may include features optimized for helping a user detect a red color. According to various embodiments, light-emitting devices may have light sources that output a spectrum optimized for helping a user detect blood. In other words, a light-emitting device may be configured to output a light spectrum that is optimized to the reflective properties of blood. A light-emitting device may also be configured to output a light spectrum optimized to cause a human's vision system to respond to blood-red colors such that the human perceives the blood-red colors as standing out in contrast to other colors. Light-emitting devices discussed herein may also provide various other features and advantages.

Light-emitting devices optimized to detect a blood-red color may be implemented in various different configurations. For example, embodiments illustrated with respect to FIGS. 1-8 and 17-23 may be referred to as additive lighting devices. In additive lighting, the light sources themselves may provide the different light colors. FIGS. 9-12, 27, 28, 32, and 33 illustrate embodiments of subtractive lighting devices. A subtractive lighting device (e.g., a device with red and green filters) may filter a broad-band light source to provide different light colors. Other lighting devices may include filters that are not necessarily specific colors, such as notch and short-pass filters (see FIGS. 27-33).

Figure 1:
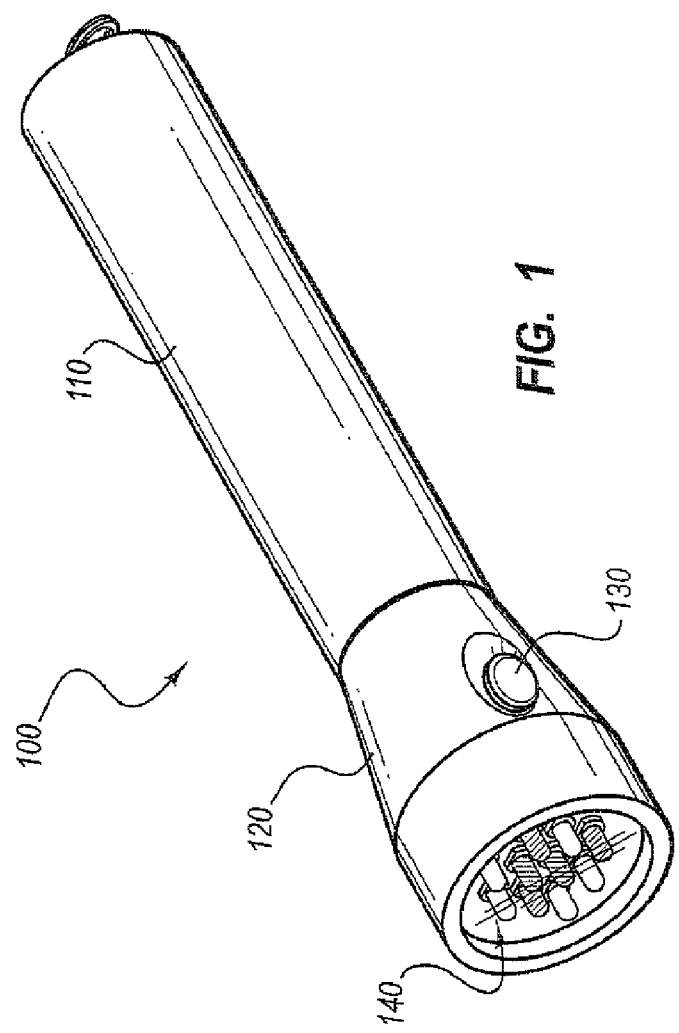
FIG. 1 is a perspective view of an exemplary light-emitting device according to certain embodiments.

FIG. 1 is a perspective view of a light-emitting device 100. Light-emitting device 100 may include a handle 110, a head 120, a button 130, and a light source 140. As illustrated in FIG. 1, light-emitting device 100 may be a hand-held flashlight. Light-emitting devices may also be wrist-worn lights, head-worn lights, ball-cap mounted lights, or any other suitable light-emitting devices. As the embodiments discussed herein illustrate, light-emitting devices may be various shapes, sizes, and configurations.

FIG. 2 is a front view of light source 140. Light source 140 may include multiple Light Emitting Diodes (LEDs). For example, light source 140 may include green LEDs 142, white LEDs 144, and red LEDs 146. When a user pushes button 130, light-emitting device 100 may turn on all the LEDs. A second push of button 130 may then turn off all the LEDs. In other embodiments, light-emitting device 100 may cycle through various modes each time a user pushes button 130. For example, when light-emitting device 100 is turned off and a user first presses button 130, green LEDs 142 may emit light. Pressing button 130 a second time may turn on red LEDs 146 such that green LEDs 142 and red LEDs 146 illuminate simultaneously. Pressing button 130 a third time may cause red LEDs 146 to begin to modulate. Pressing button 130 a fourth time may turn on white LEDs 144 and stop the modulation of red LEDs 146. Thus, after button 130 is pushed for the fourth time, all of the green LEDs 142, white LEDs 144, and red LEDs 146 in light source 140 may simultaneously emit light. Pressing button 130 a fifth time may turn off all the LEDs.

Each mode of light-emitting device 100 may provide different functions in blood tracking. For example, in the first mode, green LEDs 142 may help illuminate a hunter's path, but blood might not stand out to the hunter. In the second mode, when both green LEDs 142 and red LEDs 146 are turned on, the hunter may perceive red colors (such as blood) as standing out in contrast to non-red colors. Seeing only the green light in the first mode may contrast with the red and green lighting of the second mode in a manner that makes blood stand out to the hunter.

In the third mode, red LEDs 146 may be modulated. Modulating red LEDs 146 may simulate motion of red objects that reflect the light from red LEDs 146. The modulation of red LEDs 146 may cause the Middle Temporal (MT) region in the cortex of the brain to draw a user's attention to the motion, which may make red objects stand out to a user. The MT region of the cortex may detect smoothly changing intensities of light and send the light-intensity information to an attention portion of the brain. The attention portion of the brain may bring the changing intensities into human consciousness. Thus, modulating the red light may help focus a user's attention on red objects illuminated by light-emitting device 100.

Light emitting device 100 may modulate red LEDs 146 at various frequencies. For example, red LEDs 146 may be modulated at 1 hertz (Hz). In some embodiments, red LEDs 146 may be modulated at any suitable frequency, including frequencies greater or less than 1 Hz. An analog or digital timing circuit may modulate red LEDs 146. In other embodiments, a user may modulate red light by manually switching red LEDs 146 on and off.

In various embodiments, beams of green and red light may illuminate an area where at least a portion of the green light and at least a portion of the red light combine. The characteristics of green and red light sources may be designed such that the combination of green and red light may cause a human to perceive red colors as standing out in contrast to other colors. A red color may stand out in contrast to other colors in various different manners. For example, a red color may stand out in contrast to other colors in terms of hue, saturation, and/or brightness. In a Hue, Saturation, and Brightness (HSB) color model, any color may be completely described in terms of hue, saturation, and brightness.

Brightness may be described as a perceived luminance of an object or material. In other words, brightness may be an attribute of visual perception that describes the amount of light an object appears to emit or reflect. If a white light source shines on a red object, the red object may reflect only the spectrum of the white light that corresponds to the red color of the object. The rest of the energy in the white light may be absorbed by the object. Thus, only a small percentage of the energy in the white light may be reflected by the red object. In contrast, if a red light source shines on the red object, a higher percentage of energy from the red light source may be reflected, which may cause the red object to appear brighter and to stand out to a user.

Hue may be described as the gradation of a color. Hue may be classified as red, blue, green, or yellow in reference to the color spectrum. A background hue may induce a complementary hue in an object set against the background. For example, red is the complementary hue of green, and a green background may make a red object set against the green background appear more red. This inductive effect may be the strongest when the background is more saturated and/or brighter than the object. Thus, when a brighter green light source is used with a dimmer red light source to find blood on the ground, the ground may have a slightly green hue. The slightly green hue of the ground may induce red coloring in the blood to cause the blood to appear more red. In some embodiments, light-emitting device 100 may include more green LEDs than red LEDs to cause a background scene to have a green hue. In other embodiments, light-emitting device 100 may include the same number of red and green LEDs or more red LEDs than green LEDs. In various embodiments, a light emitting device may include a brighter or more intense green light source than red light source. In other embodiments, the brightness of the red light source may be greater than or equal to the brightness of the green light source.

In the HSB color model, saturation may refer to the purity or intensity of a specific hue. A highly saturated hue may have a vivid, intense color, while a less saturated hue may appear more muted and gray. With no saturation at all, a hue may become a shade of gray. The saturation of a color may be determined by a combination of light intensity and how much light is distributed across different wavelengths of the light spectrum. The purest color may be achieved by using a narrow-band light source at a high intensity. Thus, a narrow-band red light source centered around wavelengths reflected by blood may achieve greater saturation for blood-red colors, possibly making the blood-red colors stand out. The color of a background may also affect the apparent saturation of an object set against the background. A background may enhance saturation of objects with a complimentary hue.

Thus, a green background may enhance the saturation of red objects set against the green background.

The human eye contains three types of photoreceptor cells: red cones, green cones, and blue cones. The full spectrum of colors that a human may recognize may be an interpretation of signals sent from these three cones to a vision center in the brain's cortex (often thought to be in the area known as "V4"). Since much of the light spectrum for the red and green cones overlap, the configurations of red and non-red light sources may be chosen to minimize activation of the red cones of the retina for light reflected off objects of non-blood-red wavelengths. This maximizes the effect of the midget ganglion color-opponent cellular response for the combined red/green cone signals, which may cause the V4's color interpretation circuitry to blend perceived colors of objects away from red unless the object has a blood-red color. The discussion corresponding to FIGS. 13-16 provides additional detail about how the human vision system may respond to different wavelengths of light.

FIGS. 3-7 show various combinations of LEDs in light-source 140. FIG. 3 is a front view of light-source 140 with a red LED 146 in the middle of three green LEDs 142. FIG. 4 is a front view of light-source 140 with red LEDs 146 encircled by green LEDs 142 and white LEDs 144. FIG. 5 is a front view of light-source 140 with a red LED 146 surrounded by a square configuration of green LEDs 142 and white LEDs 144. FIG. 6 is a front view of light-source 140 with a diamond-shaped configuration of green LEDs 142 and red LEDs 146. FIG. 7 is a front view of light-source 140 with another configuration of green LEDs 142, white LEDs 144, and red LEDs 146.

As FIGS. 3-7 illustrate, light source 140 may include various different combinations of red, green, and white LEDs. Any other suitable combination of LEDs may also be implemented in light source 140. Light emitting device 100 may include various other light-sources in addition to or in place of LEDs. For example, light emitting device 100 may include one or more incandescent lights, halogen lights, fluorescent lights, xenon lights, and/or any other suitable light sources.

Light-emitting device 100 may include light sources with various different wavelengths and intensities. For example, light-emitting device 100 may include a 30 milliAmp (mA) red LED with a peak wavelength of 630 nm. A peak wavelength may be a wavelength where a radiometric emission spectrum of a light source reaches its maximum.

A bandwidth of the 30 mA red LED may be equal to or less than approximately 30 nm. A bandwidth of an LED may be a spectral line half-width of the LED. An bandwidth of an LED may also be a frequency band covering wavelengths that represent a high percentage of the energy emitted by the LED. In some embodiments, a bandwidth of the 30 mA red LED may be equal to or less than 17 nm. A field-of-view of the 30 mA red LED may be approximately 15 degrees. A field-of-view may be an angle of a vertex of a cone of light emitted by a light source. Also, the 30 mA red LED may have a luminosity of approximately 5200 millicandelas (mcd).

Light-emitting device 100 may include a 30 mA green LED with a peak wavelength of 525 nm. A bandwidth of the 30 mA green LED may be approximately equal to or less than 30 nm. A field-of-view of the 30 mA green LED may be approximately 12 degrees. The 30 mA green LED may have a luminosity of approximately 6000 mcd. Light-emitting device 100 may also include a 30 mA white LED with a 12 degree field-of-view and a luminosity of 13000 mcd. According to some embodiments, an optimal light combination may include four 30 mA white LEDs, three 30 mA green LEDs, and two 30 mA red LEDs. Light-emitting device 100 may include various other optimal light combinations.

Light-emitting device 100 may include light sources with various other peak wavelengths, bandwidths, mA ratings, fields-of-view, and luminosity ratings. For example, light-emitting device 100 may include 20 mA LEDs. Light emitting device 100 may also include LEDs with any other suitable mA rating, including ratings of greater and less than 20 mA. Light-emitting device 100 may include red LEDs with peak wavelengths that range from approximately 625 to 740 nm. However, LEDs with peaks wavelengths approaching to 740 nm may not be particularly useful because of the darkness of the red color they emit. In some embodiments, red LEDs may have peak wavelengths of 635 nm, 645 nm, or 660 nm. Light-emitting device 100 may also include red LEDs with various other suitable peak wavelengths. Light-emitting device 100 may include green LEDs with peak wavelengths that range from approximately 500 nm to approximately 565 nm. In some embodiments, green LEDs may have peak wavelengths of 540 nm or 545 nm. Light-emitting device 100 may also include green LEDs with various other suitable peak wavelengths.

Light-emitting device 100 may include LEDs or other light sources with any suitable field of view. According to some embodiments, LEDs with a field of view ranging from 12 to 30 degrees may be optimal for handheld flashlights that are used two to three feet off the ground. A smaller field-of-view may focus the light source and provide greater intensity, which may result in a light source having a greater range. In some embodiments, light-emitting device 100 may have green LEDs with greater fields-of-view than the red LEDs. Such a configuration may provide a ring of green light around a region of combined light. One advantage of this configuration may be that blood may appear to blink as it moves between the green light area and the combined light area. This apparent blinking may trigger the motion circuitry in the brain and may make blood-red colors stand out in contrast to other colors.

In some embodiments, various other combinations of LEDs colors may be included in a light-emitting device. For example, a light-emitting device may include blue and red LEDs. However, one disadvantage of using blue LEDs is that blue LEDs may tend to make colors appear to shift in color, thus making a scene appear unnatural. In some embodiments, a light-emitting device may be implemented with a light source that transmits light with both blue and green wavelengths.

Figure 8:
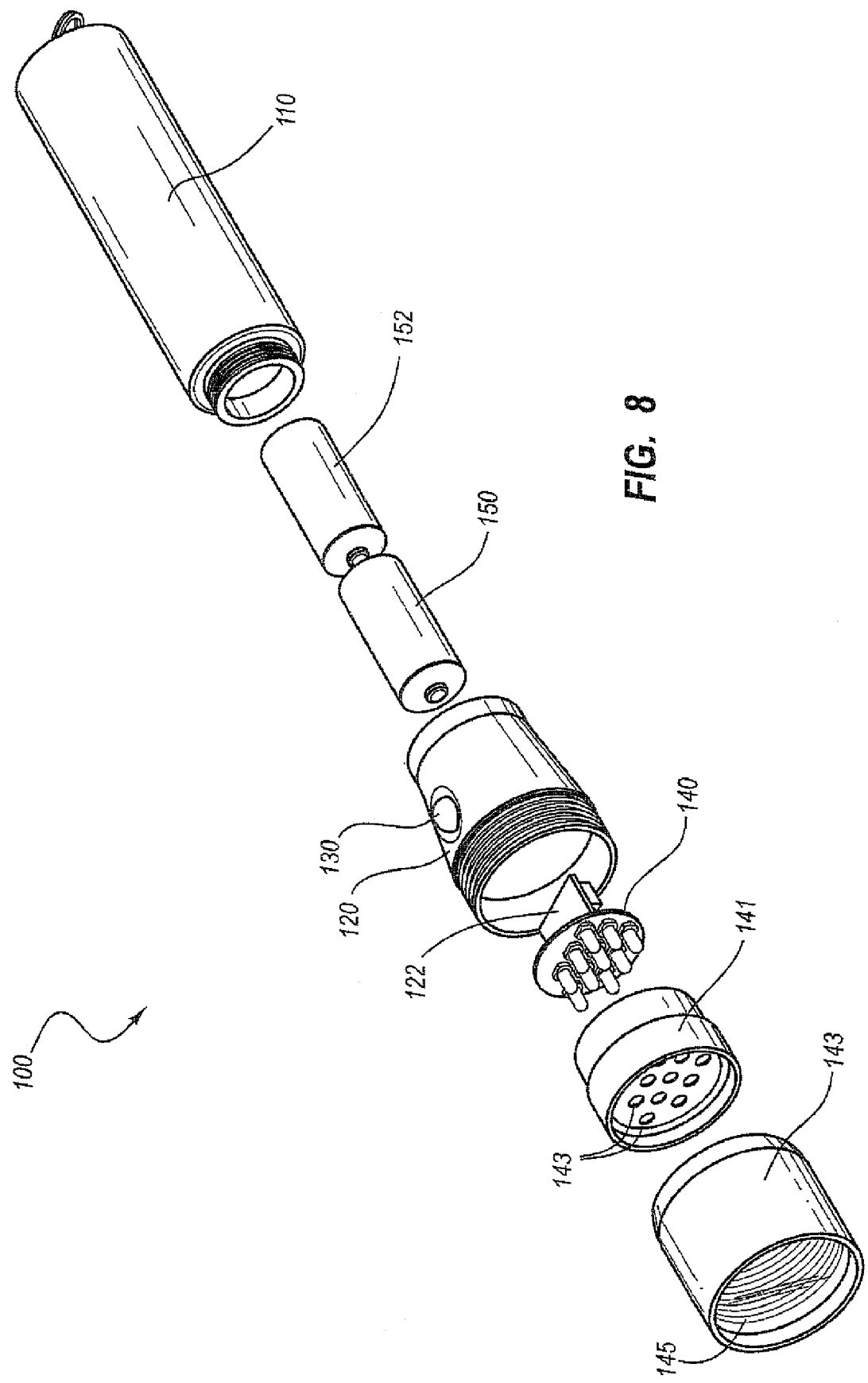
FIG. 8 is an exploded view of the exemplary light-emitting device illustrated in FIG. 1 according to certain embodiments.

FIG. 8 is an exploded view of light-emitting device 100. As illustrated, batteries 150 and 152 may fit into handle 110. A positive end of battery 150 may be coupled to a circuit board 122. Circuit board 122 may contain analog circuitry for cycling through different modes and for controlling the intensity of LEDs in light source 140. In some embodiments, circuit board 122 may contain a digital microcontroller or any other suitable digital control device. A digital microcontroller may control the different modes of light-emitting device 100 and may also control the intensities of the LEDs in light source 140.

As previously noted, head 120 may contain button 130. Head 120 may also comprise light-source 140 and a reflector 141. Reflector 141 may hold light source 140 in place, and may have apertures or openings 143 through which LEDs may extend. Head 120 may also include a cap 143, which may fit over reflector 144. Head 120 may include a protective lens 145.

Embodiments illustrated with respect to FIGS. 1-8 may be referred to as additive lighting devices. In additive lighting, the light sources themselves may provide the different light colors. FIGS. 9-12 illustrate embodiments of subtractive lighting devices. A subtractive lighting device may filter a broad-band light source to provide different light colors.

FIG. 9 illustrates a light-emitting device 200. Light-emitting device 200 may include a handle 210, a head 220, a button 230, and a filter 240. Filter 240 may include a red filter region 246 and a green filter region 244. Red filter region 246 and green filter region 244 may be transparent or translucent materials. Also, green and red filter regions 244 and 246 may be made of plastic, glass, or any other suitable filtering material. Filter 240 may also include an opaque portion 242. A light source of light-emitting device 200 may be a traditional white light source, such as an incandescent bulb, an LED, or any other suitable light source. Red filter region 246 and green filter region 244 may transmit red and green light, and the red and green light may combine to achieve various blood-illuminating features discussed in FIGS. 1-8.

In some embodiments, red and green filters may be included in an attachment that may be dimensioned to fit on light-emitting devices of various shapes and sizes. For example, as illustrated in FIG. 10, filter attachment 250 may be implemented as a cap that attaches to light-emitting device 200. Light-emitting device 200 may include threads 222, and filter attachment 250 may include threads 258. Threads 258 may screw into threads 222 to hold filter attachment 250 on light-emitting device 200. Filter attachment 250 may also include a fold-down flap 252 with a red filter 256 and a green filter 254. When flap 252 is lifted up, white light from light-emitting device 200 may pass through filter attachment 250 without being filtered. When flap 252 is placed down, white light from light-emitting device 200 may be filtered by green filter 254 and red filter 256.

Figure 11:
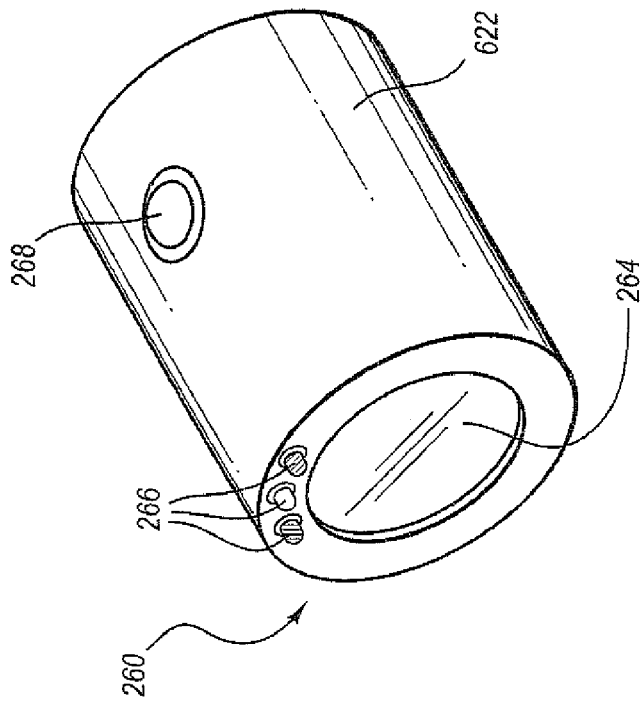
FIG. 11 is a perspective view of an exemplary filter according to certain embodiments.

FIG. 11 is a perspective view of an attachment 260 for a light-emitting device, such as light-emitting device 200. Attachment 260 may include a housing 262, a green filter 264, red LEDs 266, and a button 268. Thus, attachment 260 may combine aspects of both additive and subtractive lighting. A user may press button 268 to turn red LEDs 266 on and off. In some embodiments, button 268 may cycle through various modes. For example, if button 268 is pressed once, red LEDs 266 may turn on. When button 268 is pressed a second time, red LEDs 266 may modulate. Pressing button 268 a third time may turn off red LEDs 266.

Figure 12:
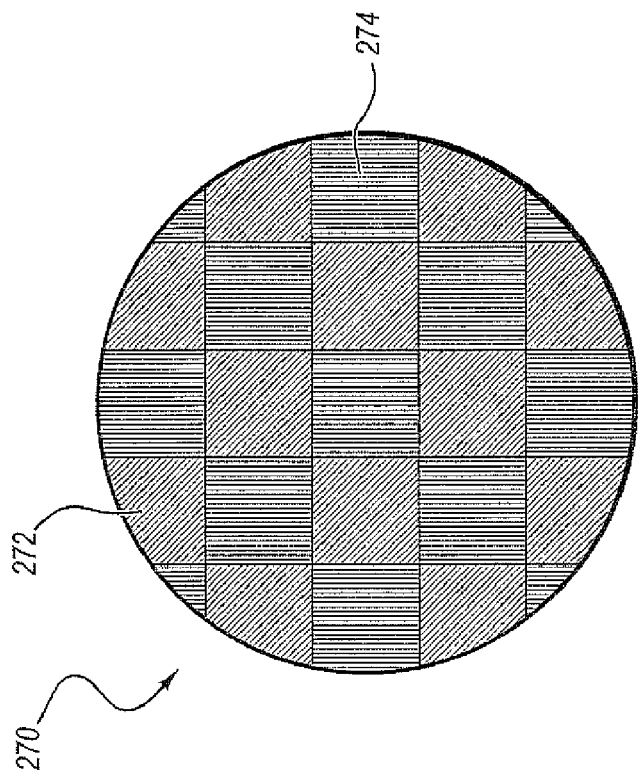
FIG. 12 is a perspective view of an exemplary filter according to certain embodiments.

FIG. 12 is a front view of a filter 270. Filter 270 may include a checkered pattern of red regions 272 and green light regions 274. Other suitable shapes, sizes, and patterns of filters may be implemented in certain embodiments. For example, the relative proportions of the green light region 274 and the red region 272 may be varied to control the relative amounts of red and green light that filter 270 transmits.

FIG. 13 is a graph showing spectral luminosity of an exemplary light-emitting device. The x-axis 302 represents the wavelength of light, and the y-axis 304 represents luminosity. In similar or identical graphs, the y-axis may represent relative sensitivity. Curve 310 may represent the luminosity of a non-red light that transmits wavelengths of light between approximately 360 nm and 565 nm. A non-red (e.g. green and blue) light source may transmit light represented by curve 310. Curve 320 may represent the luminosity of a light that transmits a narrow-band of red wavelengths centered around line 330 at 630 nm A gap 305 between non-red wavelengths of the light represented by curve 310 and red wavelengths of the light represented by curve 320 may provide contrast between blood-red objects and other objects. FIG. 14 is also a graph showing output light sensitivity for an exemplary light emitting device.

FIG. 14 is a graph showing spectral luminosity of an exemplary light-emitting device. The x-axis 354 represents the wavelength of light, and the y-axis 352 represents luminosity. Curve 360 may represent the luminosity of a green light that transmits wavelengths of light between approximately 475 nm and 565 nm. Curve 370 may represent the luminosity of a light that transmits a narrow-band of red wavelengths centered around line 380 at 630 nm.

Figure 15:
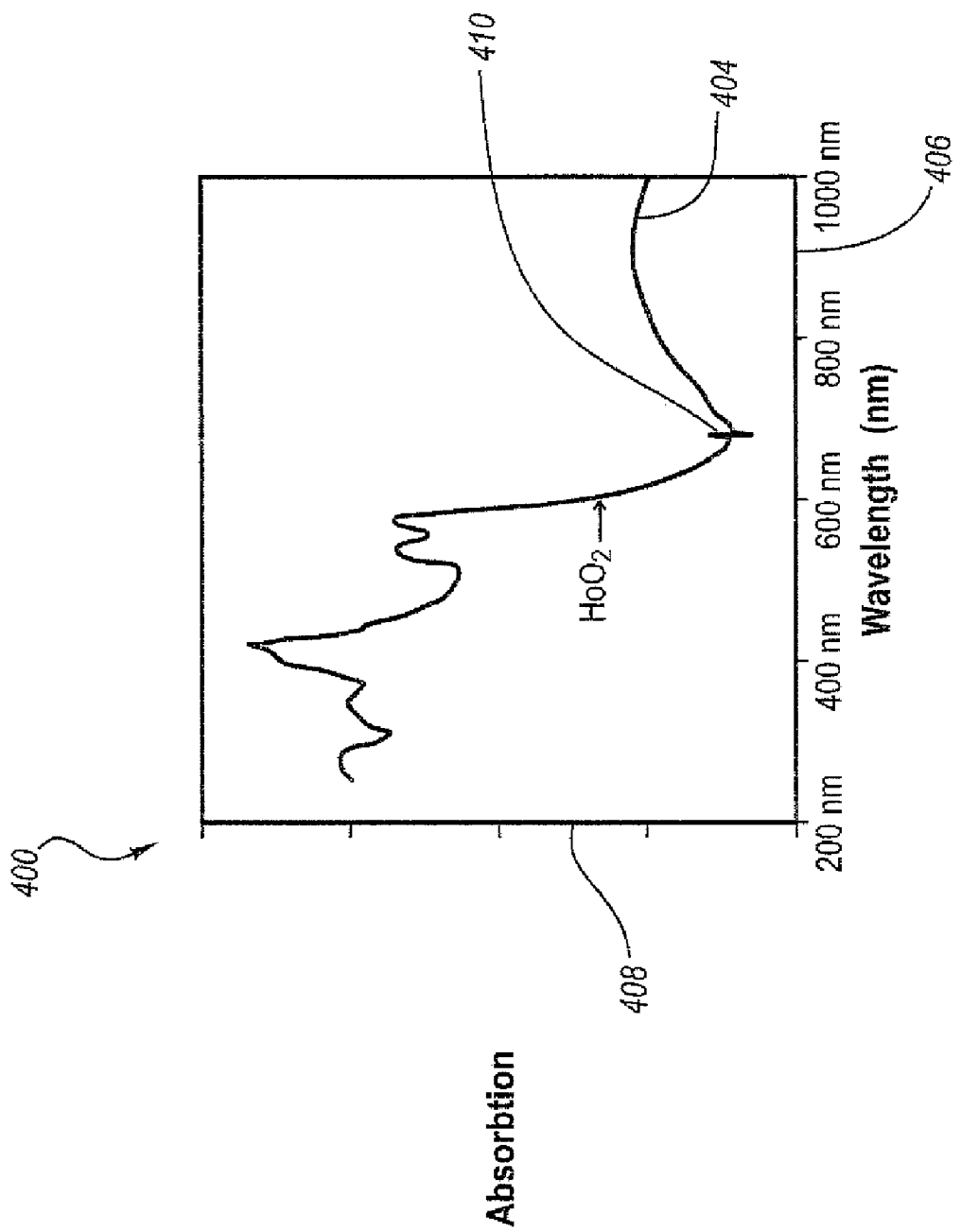
FIG. 15 is a graph of absorptivity and wavelength of hemoglobin according to certain embodiments.

According to some embodiments, a red light source may be configured to transmit light with a narrow wavelength bandwidth. For example, the light may be focused around the wavelengths reflected by blood. FIG. 15 is a graph of the absorptivity of blood hemoglobin at various frequencies and shows the frequencies where blood may be the most aborptive and the most reflective. In FIG. 15, an x-axis 406 may represent wavelengths of light, and a y-axis 408 represents absorptivity. Line 404 may represent the absorptivity of oxygenated hemoglobin. Hemoglobin may be the least absorptive at approximately 670 nm. Since absorptivity is the inverse of transmittance, hemoglobin may be the most reflective at approximately 670 nm. FIG. 15 also shows that hemoglobin has fairly reflective properties across a band of wavelengths between 620 nm and 710 nm.

Figure 16:
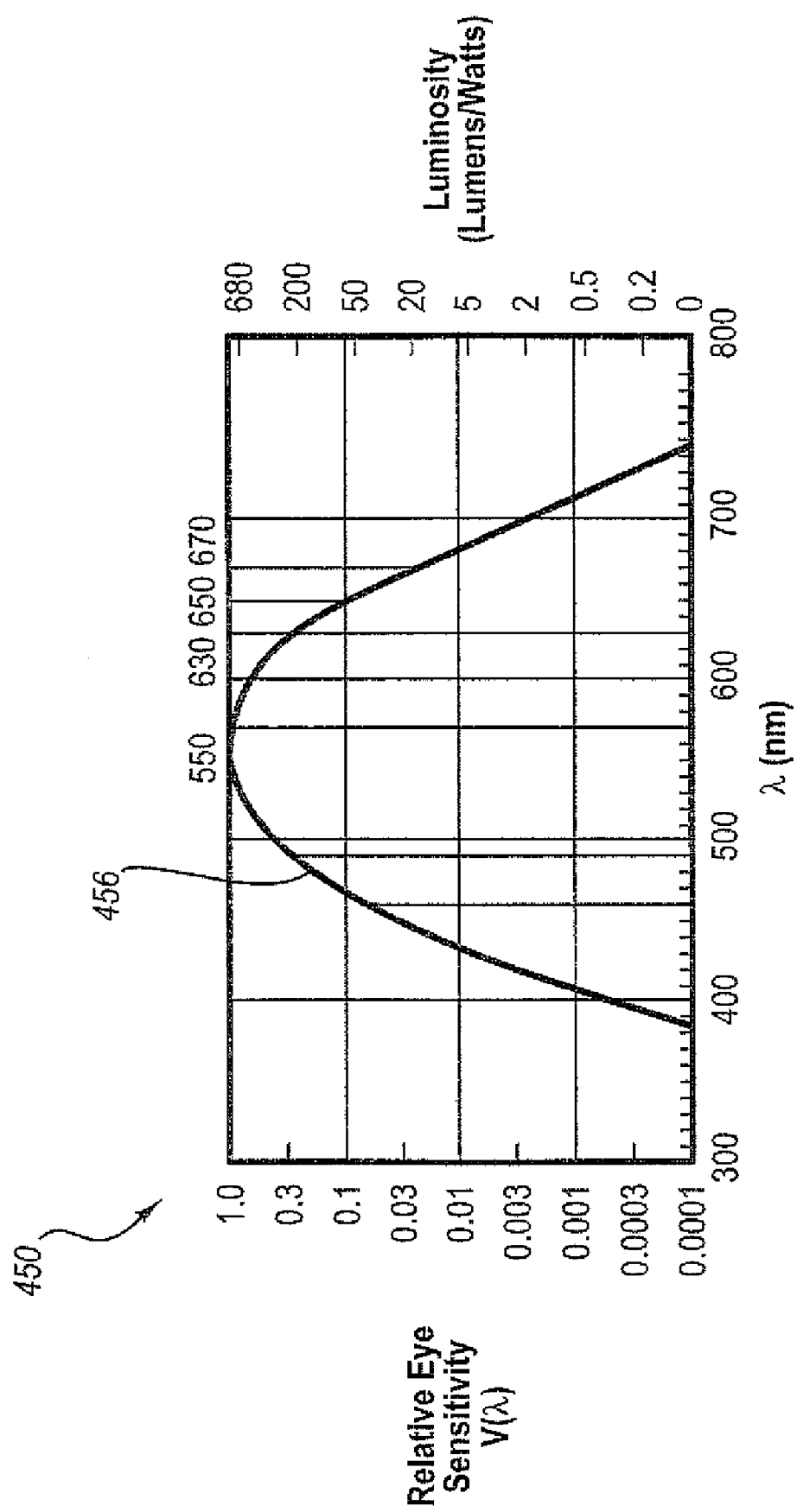
FIG. 16 is a graph of the sensitivity of the human eye to different wavelengths of light according to certain embodiments.

FIG. 16 is a graph 450 of the relative sensitivity of human vision to different wavelengths of light. Curve 456 may show the sensitivity of human vision as a function of wavelength. Human vision may have a peak sensitivity at or around 550 nm, which is within the green color band. Relative sensitivity may drop off substantially at wavelengths below 400 nm and above 700 nm. Thus, a light source centered around 670 nm (the most reflective wavelength for blood) may appear somewhat dark to a human. Accordingly, in some embodiments, an optimum peak wavelength for a blood-detecting red light source may be less than 670 nm. In other embodiments, an optimum peak wavelength for a blood-detecting red light source may be approximately 670 nm.

Figure 17:
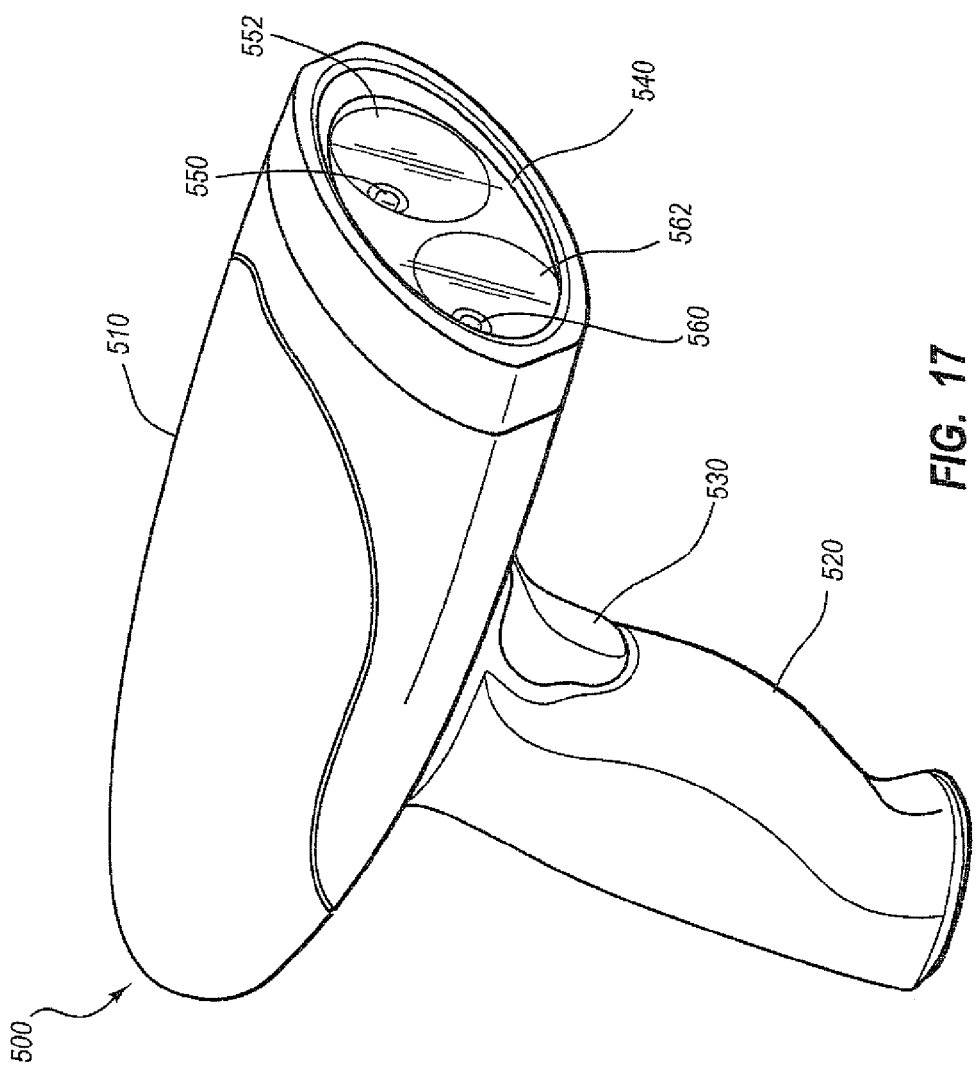
FIG. 17 is a perspective view of an exemplary light-emitting device according to certain embodiments.

FIG. 17 is a perspective view of a light-emitting device 500. FIG. 17 illustrates light-emitting device 500 with a handle 520, a trigger 530, and a head 510. Head 510 may include a lens 540 placed over a green light source 550 and a red light source 560. Green light source 550 may be held within a reflective cone 552, and red light source 560 may be held within a reflective cone 562. Reflectors 552 and 562 may focus and direct light forward through lens 540. According to some embodiments, green light source 550 may be a 3 watt LED. In some embodiments, red light source 560 may also be a 3 watt LED. Light-emitting device 500 may also include green and red light sources that are rated at any suitable wattage, include rating of more or less than 3 watts.

Figure 18:
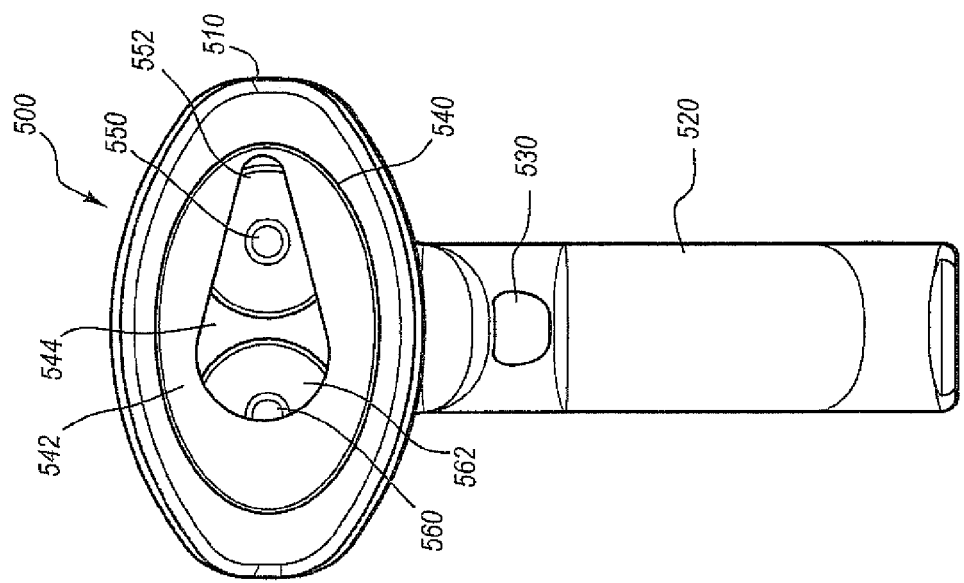
FIG. 18 is a front view of the exemplary light-emitting device illustrated in FIG. 17.

FIG. 18 is a front view of light-emitting device 500. FIG. 18 illustrates a front of trigger 530 and handle 520. FIG. 18 also illustrates a front of lens 540. Lens 540 may contain a translucent portion 542 and a clear or transparent portion 544. Translucent portion 542 may diffuse light and may be referred to as a diffuser. In some embodiments, transparent portion 544 of lens 540 may cover less than 50% of red light reflector 562. Transparent portion 544 of lens 540 may cover more than 50% of green light reflector 552. Thus, more green light than red light may pass uninhibited through lens 540.

Figure 19:
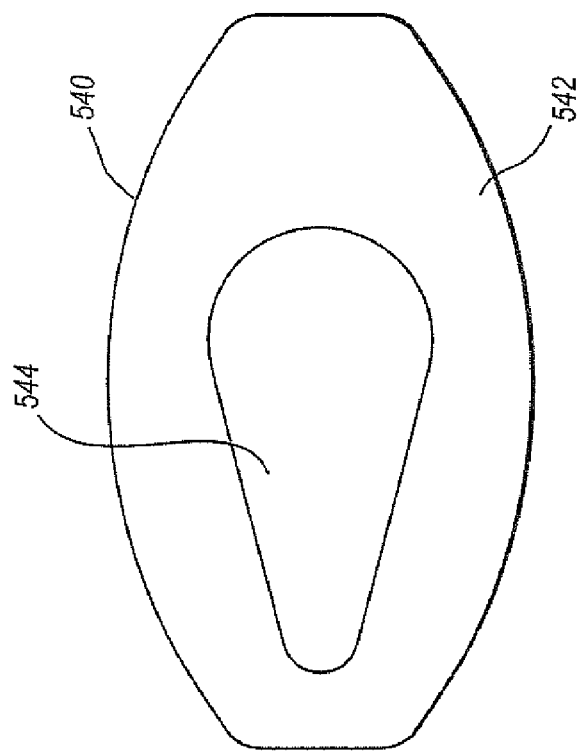
FIG. 19 is a front view of an exemplary lens of the exemplary light-emitting device illustrated in FIG. 18.

FIG. 19 illustrates lens 540 with translucent portion 542 and transparent portion 544. The shapes of lens 540, translucent portion 542, and transparent portion 544 may be designed to result in a combination of red and green light that is optimized for tracking blood. The red and green light that shines through lens 540 may combine to form a combined light area, and the combined light area may have a trapezoidal or pear shape, similar to the shape of clear portion 544. In some embodiments, translucent portion 542 may be frosted or etched in a manner that diffuses light. The amount of green and red light that shines though lens 540 may be controlled by the opacity of the diffusing material or etching of translucent portion 542.

Figure 20:
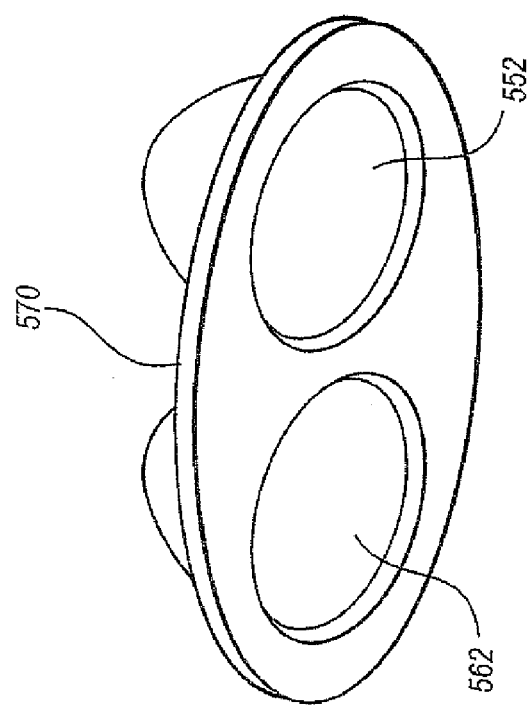
FIG. 20 is a perspective view of a reflector of the exemplary light-emitting device illustrated in FIG. 17.
Figure 21:
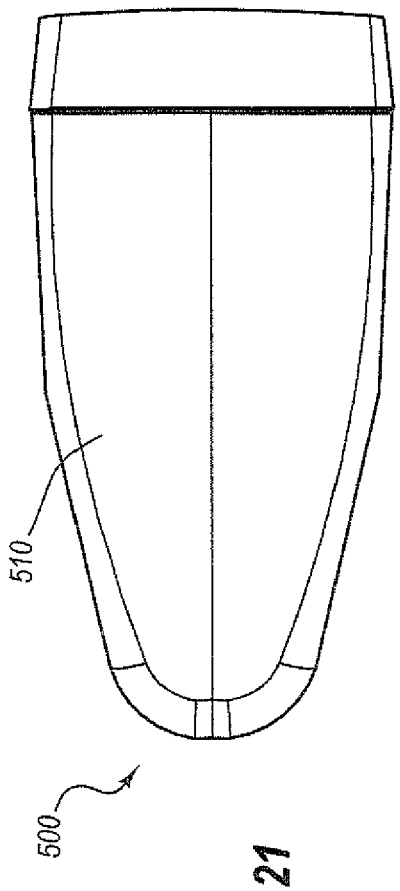
FIG. 21 is a top view of the exemplary light-emitting device illustrated in FIG. 17.
Figure 23:
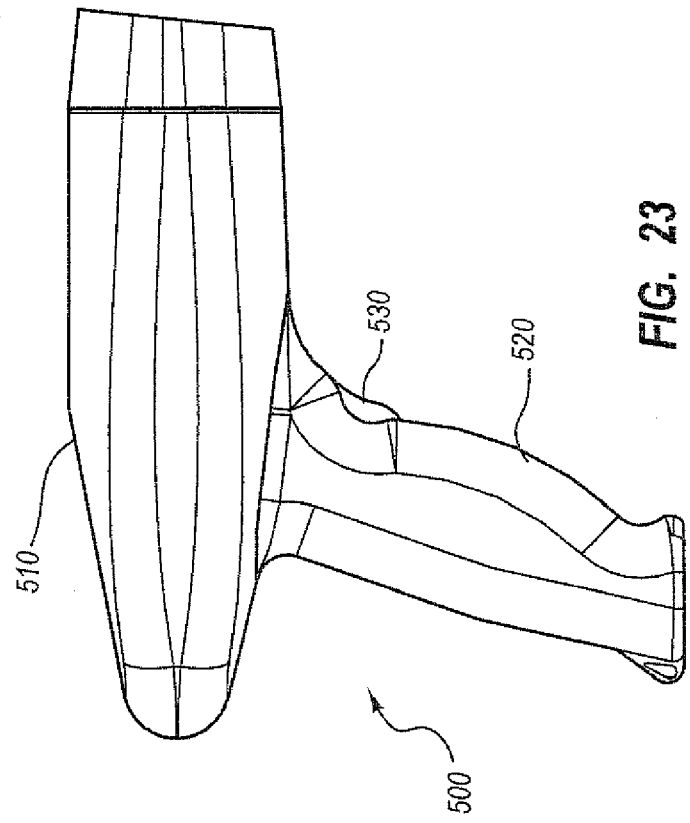
FIG. 23 is a side view of the exemplary light-emitting device illustrated in FIG. 17.
Figure 22:
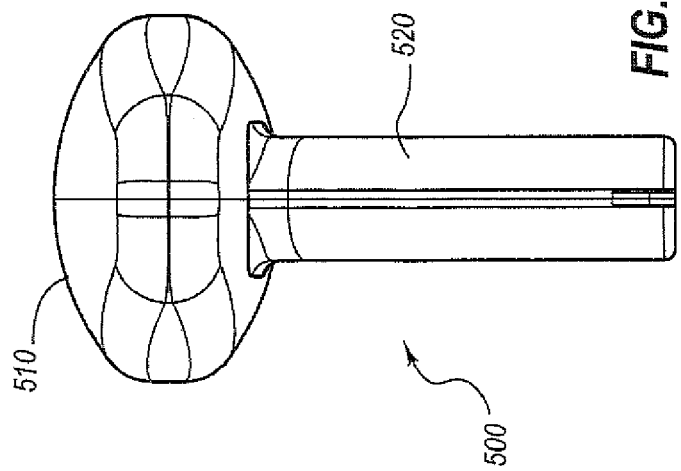
FIG. 22 is a back view of the exemplary light-emitting device illustrated in FIG. 17.

FIG. 20 illustrates a reflector 570 with reflector cones 552 and 562. Reflector cones 552 and 562 may direct and focus light sources placed within them. Reflector 570 may also comprise various other shapes with cones of any suitable shape or size. FIGS. 21-23 illustrate a body of light-emitting device 500. FIG. 21 is a top view of light-emitting device 500 and shows a top portion of head 510. FIG. 22 is a back view of light-emitting device 500 and shows a back portion of head 510 and handle 520. FIG. 23 is a side view of light-emitting device 500 and shows a side view of head 510, trigger switch 530, and handle 520.

Figure 24B:
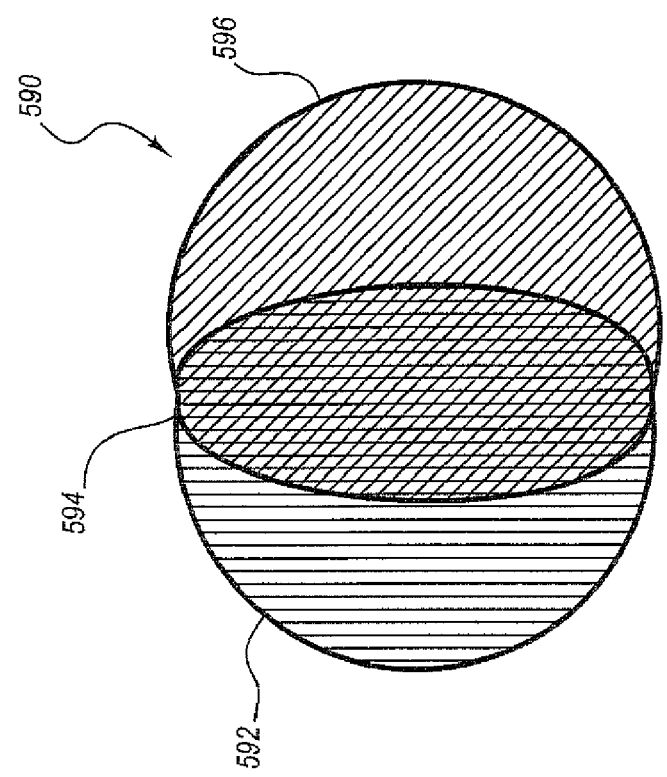
FIG. 24B is a top view of a pattern of green and red light according to certain embodiments.
Figure 24A:
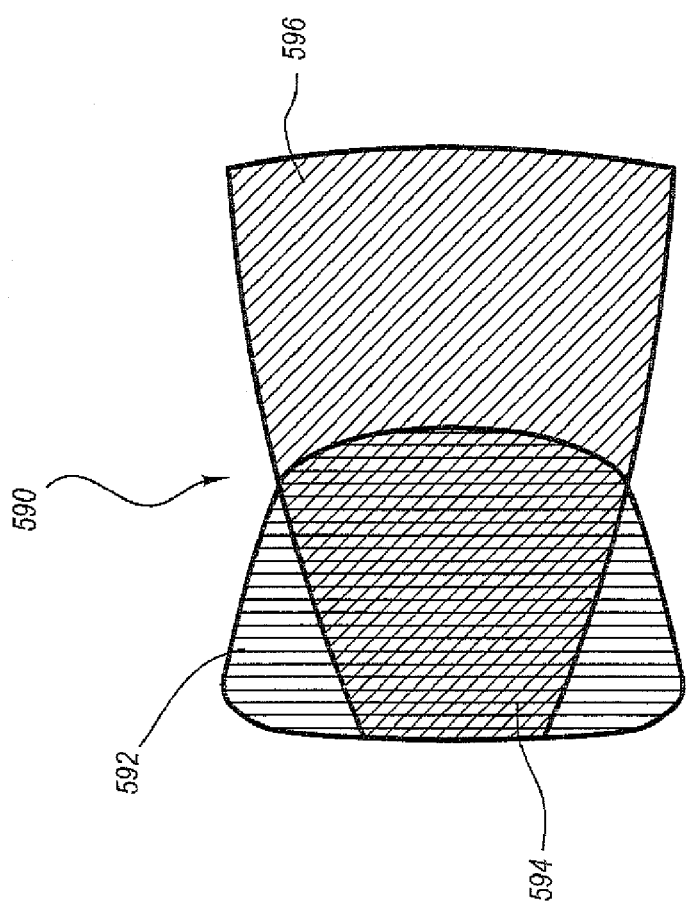
FIG. 24A is a top view of a pattern of green and red light according to certain embodiments.

FIG. 24A shows a pattern of light 590 that may be emitted by light emitting device 500. In some embodiments, pattern 590 may be visible when light emitting device 500 shines on a scene a few feet away, but may not be visible at greater distances. In some embodiments, pattern 590 may be visible at greater distances. Section 592 of pattern 590 may be red light, section 596 of pattern 590 may be green light, and section 594 of pattern 590 may be a mix of red and green light. In some embodiments, blood-red objects illuminated by section 594 may stand out in contrast to non-blood-red objects illuminated by section 594. According to certain embodiments, light-emitting device 500 may be designed such that pattern 590 may be other suitable shapes and/or sizes.

According to certain embodiments, FIG. 24A may generally represent a pattern 590 projected by light-emitting device 500 onto a flat surface perpendicular to a direction of a beam of light emitted by light-emitting device 500. In other words, when light-emitting device 500 shines light on a flat surface parallel to a plane of lens 540, the light may form pattern 590. Pattern 590 may be visible when light-emitting device 500 is approximately two to three feet or less from the flat surface. As shown, pattern 590 may comprise a rounded-trapezoidal pattern of red light and a rounded-trapezoidal pattern of green light. The intersection of the green and red light patterns may result in a rounded-trapezoidal pattern of combined light. Rounded trapezoidal patterns may also be referred to as truncated-conical patterns and may appear to be truncated pieces of pie with rounded sides. Pattern 590 as a whole may appear to be tail-fin shaped (e.g., similar in shape to fish tail, helicopter tail, etc.).

FIG. 24B shows pattern of light 590 at a greater distance. At a greater distance, mixed light section 594 may be a relatively small portion of pattern 590, and green light section 596 may be the largest color portion in pattern 590. The shape of pattern 590 in FIG. 24B may provide various advantages for tracking and detecting blood-red colors. For example, since green may be a dominant color in pattern 590, a user's eye may adjust to seeing the color green as the user scans a scene for blood. When the user moves light-emitting device 500 so that pattern 590 shines on blood, the blood may not stand out if only green light section 596 or red light section 592 shine on the blood. However, as soon as mixed light section 594 shines on the blood, the blood may immediately stand out to the user. After a short time however, the user's eye may compensate for the blood's reflection of the mixed light colors, and blood may not stand out to the user as much. Thus, a smaller mixed light section, such as mixed light section 594, may allow a user to make small movements of pattern 590 to move blood in and out mixed light section 594.

Some advantages of a pattern with the shape of pattern 590 may be described in terms of cool and hot colors. As previously mentioned, before mixed light section 594 of pattern 590 illuminates blood, a user's eyes may become adjusted to green, which may be considered a cool color. As soon as mixed light section 594 illuminates a blood-red color (which may be considered a hot color), the blood-red color may jump out to a user because of the contrast between the hot color (blood red) and the cool color (green).

According to certain embodiments, FIG. 24B may generally represent a pattern projected by light-emitting device 500 onto a flat surface perpendicular to a direction of a beam of light emitted by light-emitting device 500. In other words, when light-emitting device 500 shines light on a flat surface parallel to a plane of lens 540, the light may form pattern 590. Pattern 590 may be visible when light-emitting device 500 is approximately two to three feet or more from the flat surface. As shown, pattern 590 may comprise two circular patterns of light that intersect to form an elliptical shape of mixed light. The mixed light region may also be referred to as being football shaped.

Figure 25:
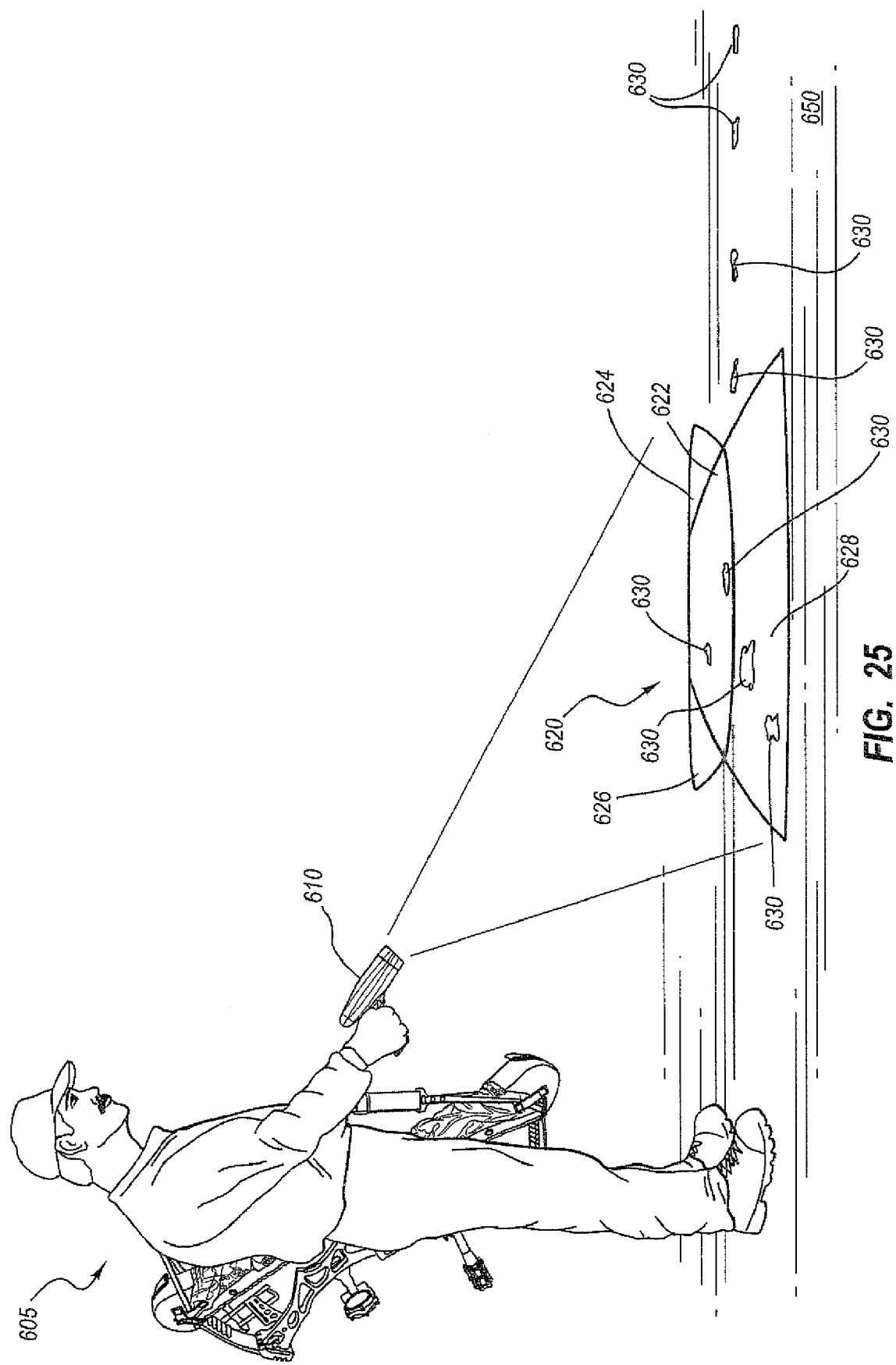
FIG. 25 is a scene illustrating an exemplary use of a light-emitting device according to certain embodiments.

FIG. 25 shows a hunter 605 using a light-emitting device 610. Although a hunter is shown in the FIGS., it is to be understood that any of the disclosed embodiments may be used by any other user group, including without limitation persons involved in law enforcement, crime scene investigation, and the like. Light-emitting device 610 may illuminate a lighted region 620 on ground 650. Lighted region 620 may include red regions 624 and 626, a green light region 628, and a combined light region 622. Hunter 605 may be tracking a trail of blood 630 left by a wounded animal (not shown). The properties of combined light region 622 may make blood 630 stand out in contrast to other objects in combined light region 622. Thus, light-emitting device 610 may help hunter 605 more easily track the trail of blood 630. Device 610 may also project a beam of light sufficient to allow the hunter to see blood from a greater distance (e.g., with the person in an upright position) as compared to another, less powerful light that may require a closer distance (e.g., with the person bent over or on his hands and knees).

FIG. 26 is a scene of hunter 605 using a light-emitting device 612. Light-emitting device 612 may illuminate a lighted region 620 on ground 650. As shown in FIG. 26, hunter 605 may scan ground 650 looking for a trail of blood 630. Scanning the ground with light-emitting device 612 may cause blood 630 to appear to blink, which may make blood 630 stand out to hunter 605 in contrast to leaves, twigs, dirt, or other objects.

Figure 28:
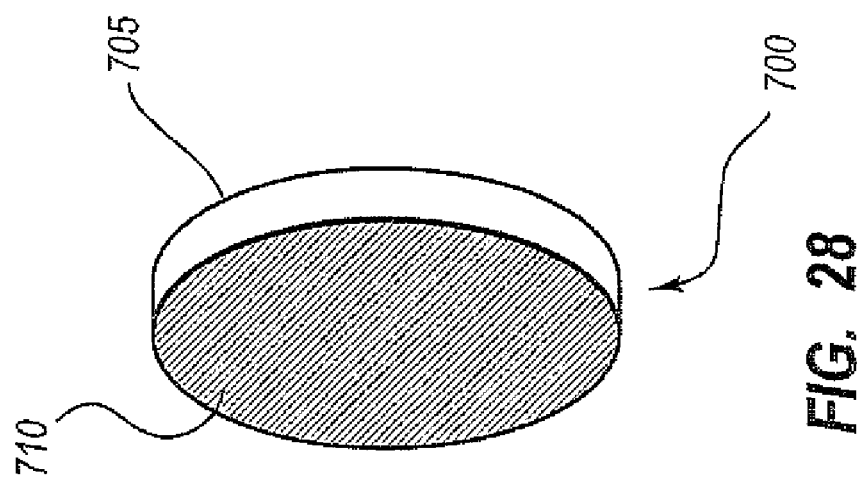
FIG. 28 is a perspective view of an exemplary filter according to certain embodiments.
Figure 27:
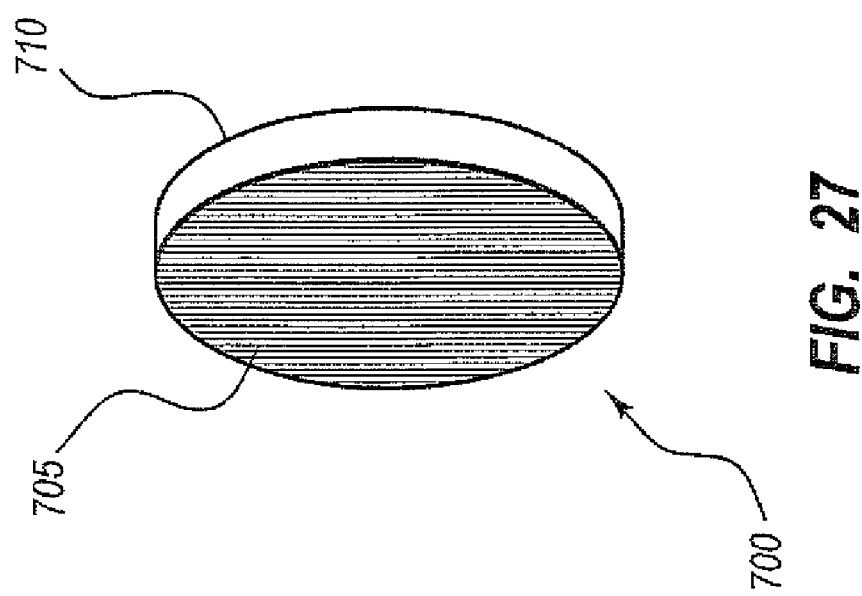
FIG. 27 is a perspective view of an exemplary filter according to certain embodiments.
Figure 30:
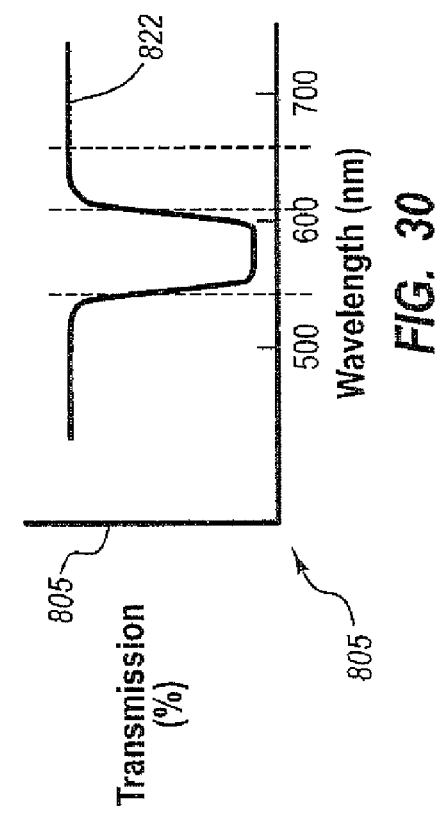
FIG. 30 is an exemplary graph of light filtered by the filter shown in FIG. 28.
Figure 29:
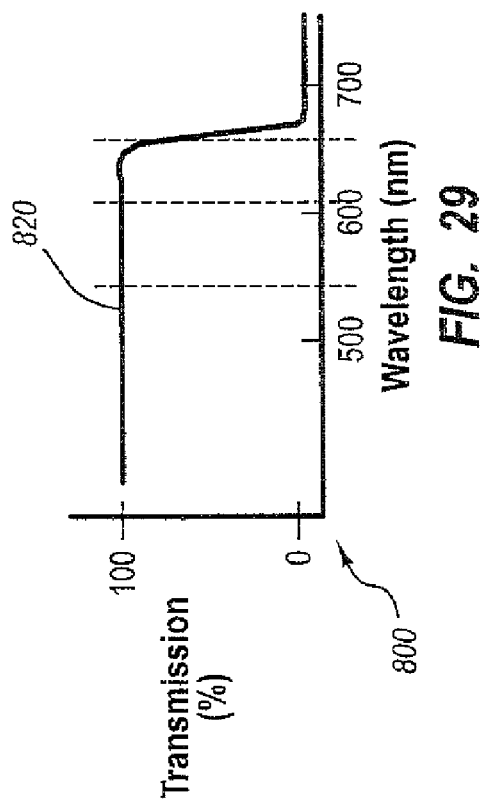
FIG. 29 is an exemplary graph of light filtered by the filter shown in FIG. 27.
Figure 31:
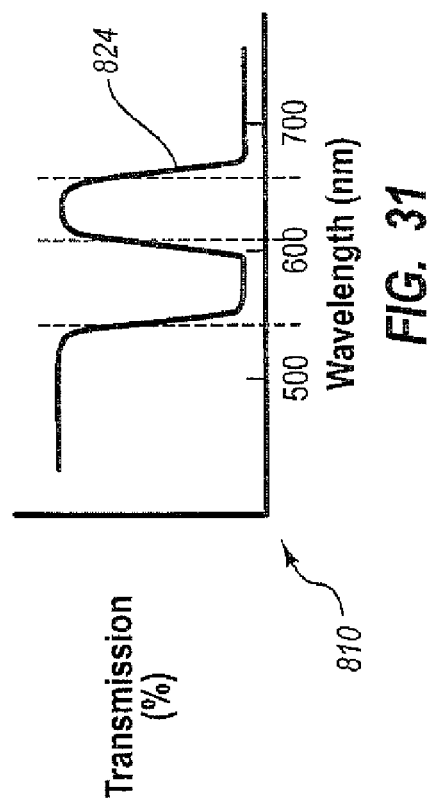
FIG. 31 is an exemplary graph of the light filtered by a combination of the filters shown in FIGS. 27 and 28.

FIGS. 27 and 28 illustrate a lens 700. Lens 700 may be an etched glass filter. In some embodiments, lens 700 may be made of any other suitable material, such as polycarbonate. As shown in FIG. 27, a front side 705 of lens 700 may be etched or coated with a short-pass filter. A short-pass filter may be a filter that passes relatively short wavelengths (i.e., high frequencies). In some embodiments, lens 700 may comprise a long-pass filter. In various embodiments, the short-pass filter may be manufactured by using optical coatings with dielectric materials. For example, filters may be manufactured by physical vapor deposition, sputtering, or any other suitable manufacturing method. FIG. 29 is a graph 800 that represents an example of a response curve 820 for the short-pass filter. As shown in FIG. 28, a back side 710 of lens 700 may be etched or coated with a notch filter. FIG. 30 is a graph 805 that represents an example of a response curve 822 for the notch filter. As shown in FIGS. 27 and 28, the notch filter and the short-pass filter may be located on opposite sides of lens 700. Thus, lens 700 may filter light in a manner that combines the responses of the short-pass filter and the notch filter. FIG. 31 is a graph 810 with a curve 824 that represents an example of a response curve of a combination of the short-pass and notch filters. Lens 700 may be etched or coated with short-pass and notch filters that have any other suitable response curve. In some embodiments, lens 700 may be etched or coated with only a notch filter.

Lens 700 may include filters that may be used with any suitable light sources, including incandescent lights, xenon lights, halogen lights, and krypton lights. As previously mentioned, lens 700 may filter a light source to produce the light spectrum represented by line 824 in FIG. 31. In some embodiments, lens 700 may filter a light source to produce any suitable light spectrum, including the light spectrum illustrated by line 822 in FIG. 30. In some embodiments, lens 700 may be a lens of a light-emitting device, such as a handheld flashlight. In other embodiments, lens 700 may be included in an aftermarket attachment designed for use with traditional light-emitting devices.

According to various embodiments, a filter may include two lenses instead of a single lens with filters on each side. In a two lens embodiment, one lens may include a short-pass filter and the other lens may include a notch filter. In other words, the notch and short-pass filters may be manufactured on two different lenses. The lenses may be positioned in a overlapping manner (e.g., stacked on one another) to provide a filtering response similar to the response illustrated in FIG. 31. In some embodiments, the notch and short-pass filters may be manufactured on opposite sides of a single lens or on the same side of a single lens.

The properties of lens 700, or any other light filter according to embodiments discussed herein, may be designed based on the type of broadband light source that may be filtered. For example, incandescent lights may have a significant percentage of their light energy concentrated in red and green portions of the light spectrum. In contrast, white LEDs may have more energy concentrated in the blue portion of the spectrum. Thus, a filter for an incandescent light may need to be designed differently than a filter for an LED to achieve a particular desired response.

FIGS. 29-31 may represent responses for various filters and filter devices. For example, as previously mentioned, FIG. 30 may represent a notch filter. As illustrated, the notch filter may be configured to pass a red wavelength of light and a green wavelength of light. According to some embodiments, a red wavelength of light may be any wavelength between approximately 600 nm and approximately 740 nm. A green wavelength of light may be any wavelength between approximately 500 nm and approximately 580 nm. In some embodiments, the notch filter may pass a band of wavelength of red light and a band of wavelengths of green light.

The notch filter may also be configured to block a wavelength of light between a red wavelength of light and a green wavelength of light. The wavelength of light that is blocked may be a red wavelength, a green wavelength, or any wavelength between red and green wavelengths of light. In some embodiments, the notch filter may be configured to block a band of light. A filter may be said to block a wavelength if the filter attenuates the wavelength more than it attenuates other wavelengths. Thus, a filter may block a wavelength without completely attenuating the wavelength. On other hand, a filter may be said to pass a wavelength if the filter attenuates the wavelength less than it attenuates other wavelengths. Thus, a filter may pass a wavelength while still providing some attenuation for the wavelength.

As previously noted, FIG. 29 illustrates a short-pass filter. A short-pass filter may be configured to pass the first red wavelength of light and block a second red wavelength of light. Typically, a short-pass filter may be designed to block a band of low frequency light, such a band of red light. Short-pass and notch filters may be arranged in a checkered pattern, as shown in FIG. 12. Short-pass and notch filters may also be combined on a lens as ring-shaped circular filters that are concentric with one another. In various embodiments, the circular filters may not be concentric with one another.

In some embodiments, an optimal filter may pass wavelengths below 550 nm and may pass wavelengths between 600 nm and 670 nm. The filter may also block wavelengths between 550 nm and 600 nm and may block wavelengths above 670 nm. In various embodiments, an optimal filter may pass wavelengths below 525 nm and may pass wavelengths between 610 and 650 nm. The filter may also block wavelengths between 525 nm and 610 nm and block wavelengths above 650 nm.

Figure 33:
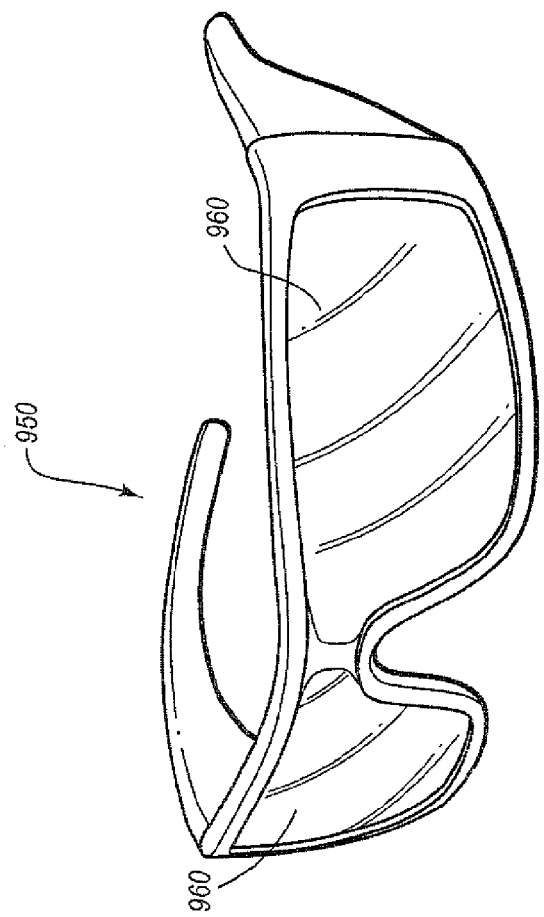
FIG. 33 is a perspective view of an exemplary pair of filtering glasses according to certain embodiments.
Figure 32:
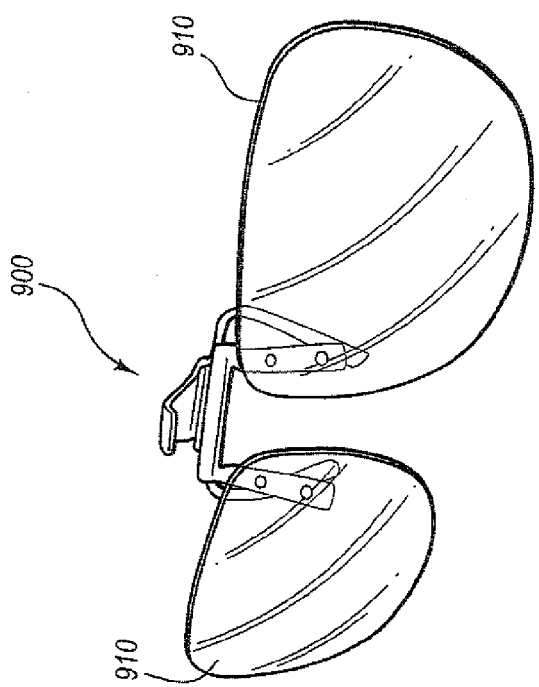
FIG. 32 is a perspective view of an exemplary clip-on glasses filter device according to certain embodiments.

FIG. 32 is a perspective view of clip-on glasses 900 with filtering lenses 910 according to certain embodiments. Lenses 910 may be etched or coated with short-pass and notch filters, as previously described with respect to lens 700. FIG. 33 is a perspective view of a pair of glasses 950 with filtering lenses 960. Like lenses 910, lenses 960 may be etched or coated with short-pass and notch filters. In certain embodiments, various other suitable filters may be incorporated into glasses.

Figure 34:
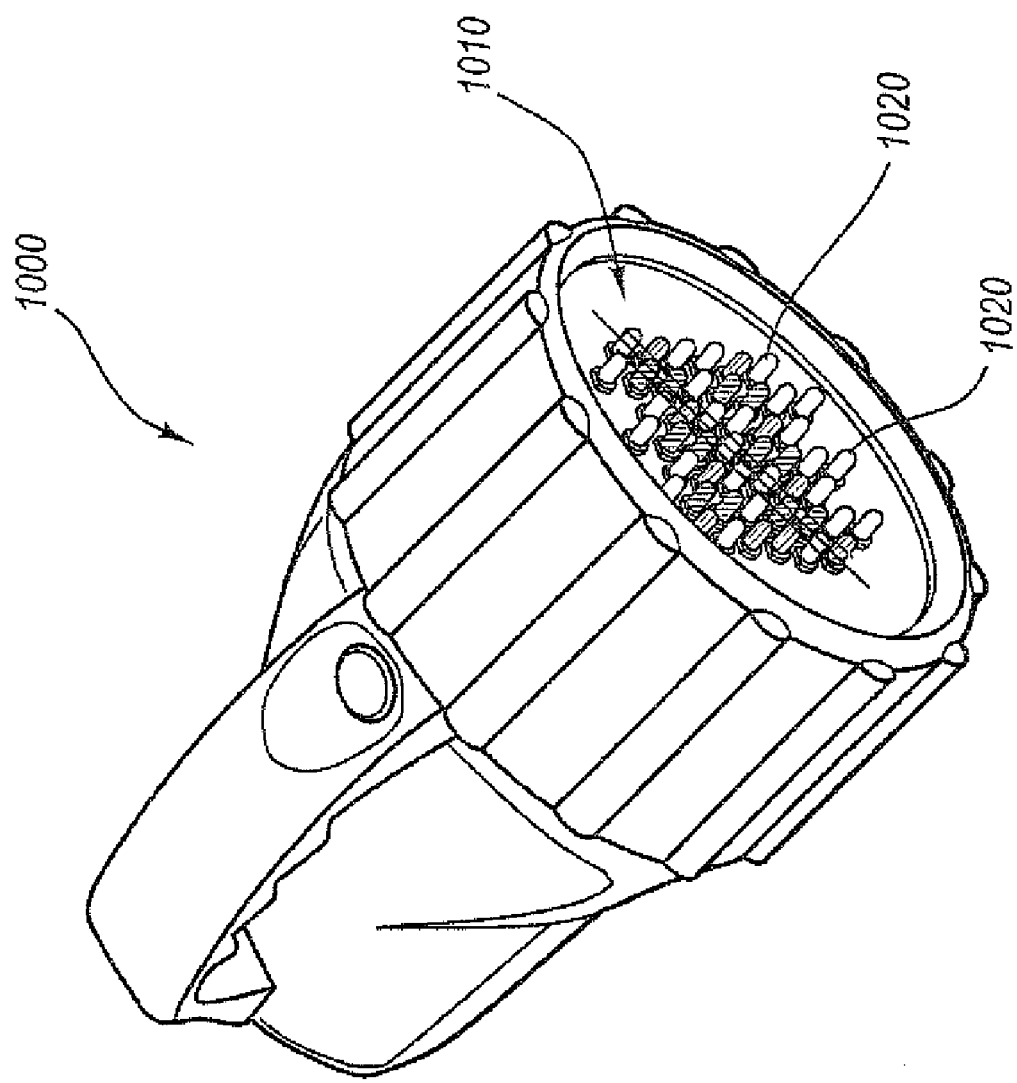
FIG. 34 is a perspective view of an exemplary light-emitting device according to certain embodiments.

FIG. 34 illustrates a high-powered light-emitting device 1000 according to certain embodiments. A light source 1010 of light-emitting device 1000 may include numerous LEDs 1020. In some embodiments, light-emitting device 100 may include 44 LEDs 1020 (20 white LEDs, 14 green LEDs, and 10 red LEDs). Light emitting device 1000 may also include various other numbers and combinations of LEDs.

Figure 36:
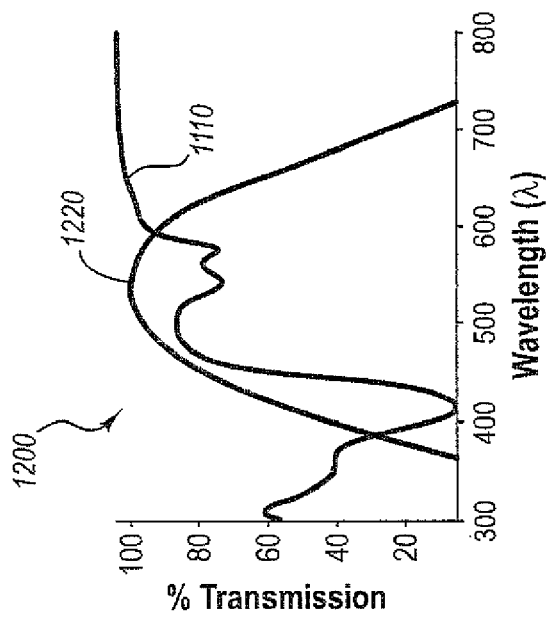
FIG. 36 is an exemplary graph of the sensitivity of the human eye to different wavelengths of light according to certain embodiments.
Figure 37:
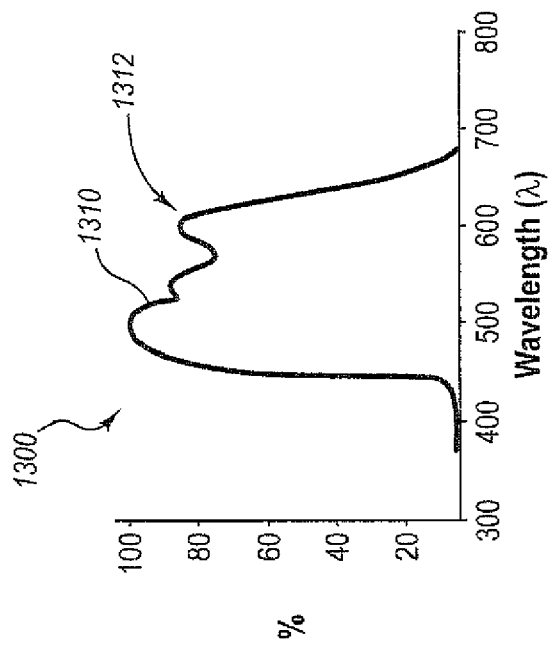
FIG. 37 is an exemplary graph of the product of data illustrated in FIGS. 35 and 36.
Figure 35:
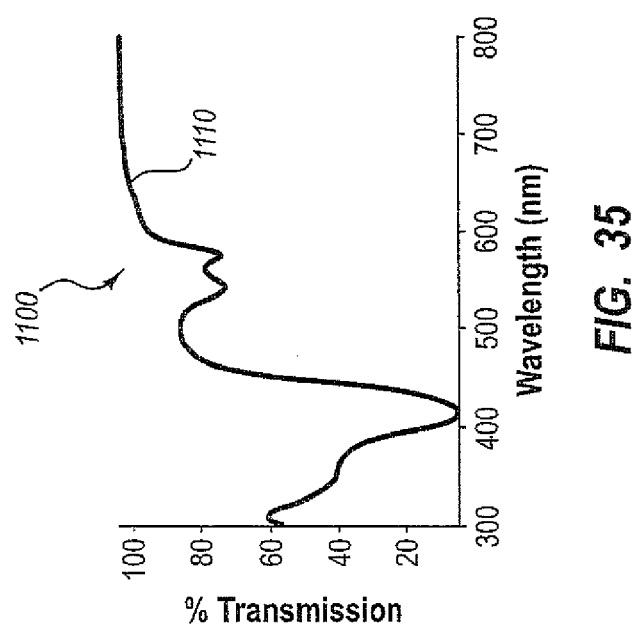
FIG. 35 is an exemplary graph of the transmittance of blood according to certain embodiments.

FIGS. 35-37 are additional graphs representing blood transmittance and relative eye sensitivity according to some embodiments. FIG. 35 is a graph 1100 with a line 1110 that may represent the transmittance of blood relative to wavelength. FIG. 36 is a graph 1200 with a line 1220 that may represent the relative sensitivity of a human eye to different wavelengths of light. FIG. 36 also shows line 1110 interposed over line 1220. FIG. 37 is a graph 1300 of a line 1310 that shows a result of the product (i.e., multiplication) of lines 1110 and 1220. Line 1310 may show a bump 1312 or increase in transmittance at or around 600 nm to 620 nm. Bump 1312 may represent frequencies where the human eye is particularly sensitive to wavelengths of light reflected by blood. Thus, in some embodiments, filters or lights may be designed to emit or transmit peak wavelengths from 600 nm to 620 nm.

Figure 38A:
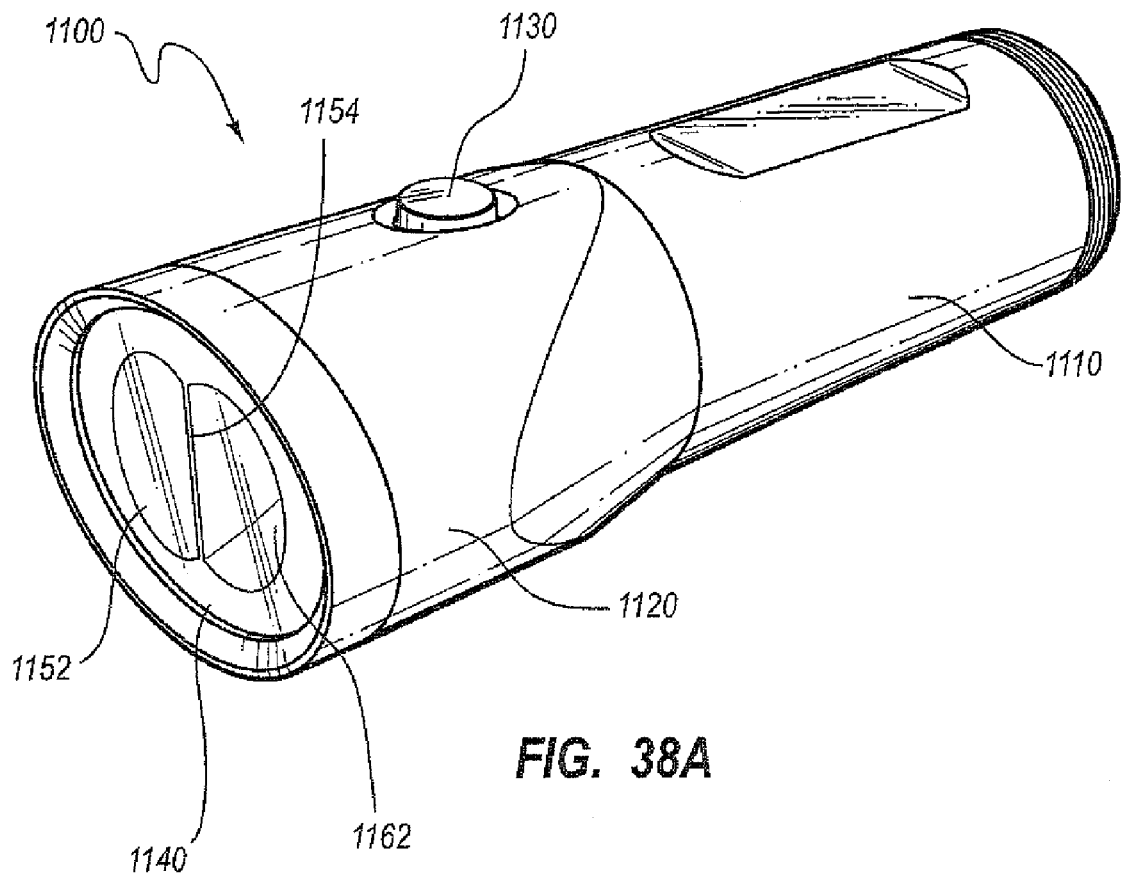
FIG. 38A is a perspective view of an exemplary light-emitting device according to certain embodiments.
Figure 38B:
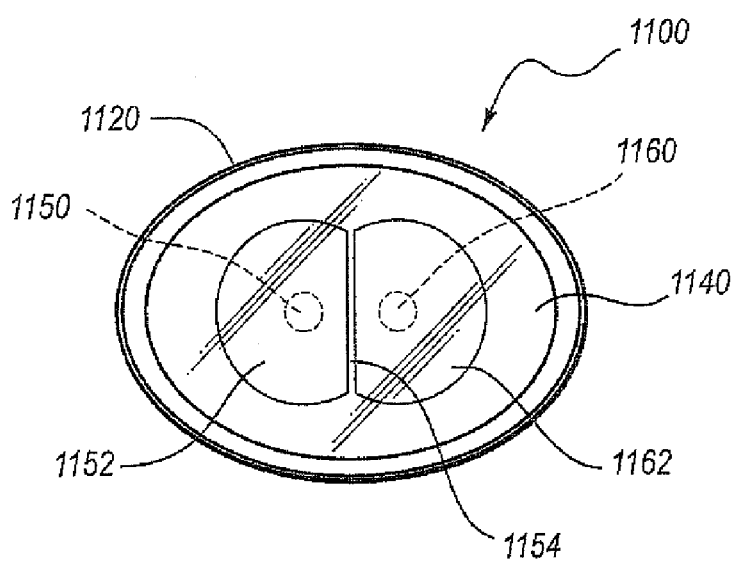
FIG. 38B is a front view of an exemplary light-emitting device according to certain embodiments.

FIGS. 38A-38B illustrate a light-emitting device 1100 according to various embodiments. As shown in these figures, light-emitting device 1100 may comprise a handle 1110, a head 1120, and a button 1130. Head 1120 may include a lens 1140 disposed over a green light source 1150 within a reflector 1152 and a red light source 1160 within a reflector 1162, as shown in FIG. 38B. Reflectors 1152 and 1162 may focus and direct light forward through lens 1140.

In various embodiments, light emitting device 1110 may comprise a divider 1154 between reflector 1152 and reflector 1162. As shown in FIGS. 38A and 38B, divider 1154 may comprise a flattened or substantially flattened member configured to separate and/or direct light emitted by green light source 1150 and/or red light source 1160. As illustrated in FIG. 38B, green light source 1150 and red light source 1160 may be positioned within relatively close proximity to each other.

Figure 39A:
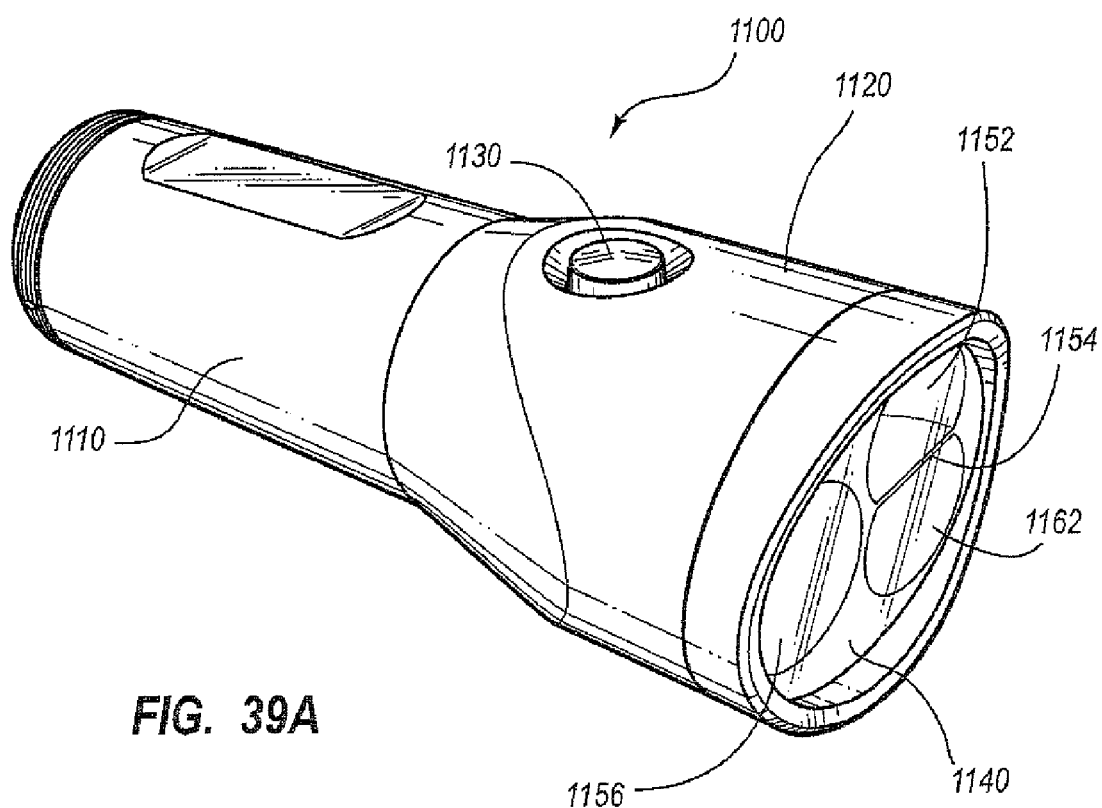
FIG. 39A is a perspective view of an exemplary light-emitting device according to certain embodiments.
Figure 39B:
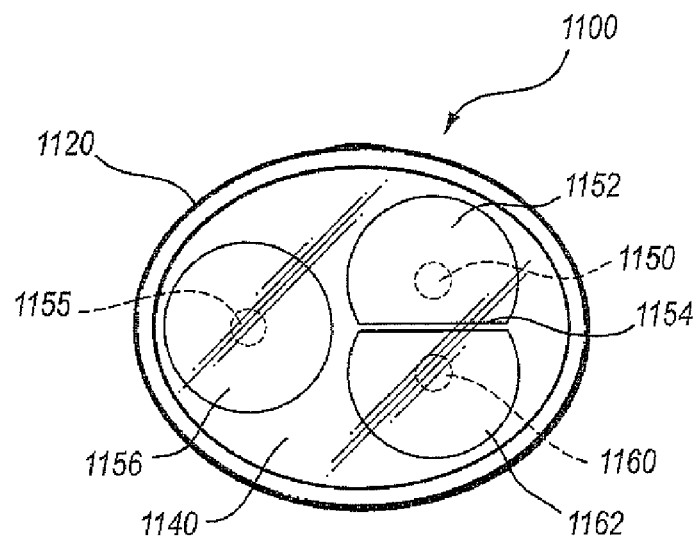
FIG. 39B is a front view of an exemplary light-emitting device according to certain embodiments.

FIGS. 39A-39B illustrate a light-emitting device 1100 according to additional embodiments. As shown in these figures, light-emitting device 1100 may comprise a handle 1110, a head 1120, and a button 1130. Head 1120 may include a lens 1140 disposed over a green light source 1150 within a reflector 1152, a red light source 1160 within a reflector 1162, and a white light source 1155 within a reflector 1156, as shown in FIG. 39B. Reflectors 1152 and 1162 may focus and direct light forward through lens 1140. White light source 1155 may be used in various situations, such as, for example, in situations where light is needed for illumination rather than for blood trailing. White light source 1155 may be used alone or in combination with green light source 1150 and/or red light source 1160. White light source may comprise light having any wavelength suitable for visual illumination of an area.

Additionally, light emitting device 1110 may comprise a divider 1154 between reflector 1152 and reflector 1162. As shown in FIGS. 39A and 39B, divider 1154 may comprise a flattened or substantially flattened member configured to separate and/or direct light emitted by green light source 1150 and/or red light source 1160. As illustrated in FIG. 39B, green light source 1150 and red light source 1160 may be positioned within relatively close proximity to each other.

Figure 40:
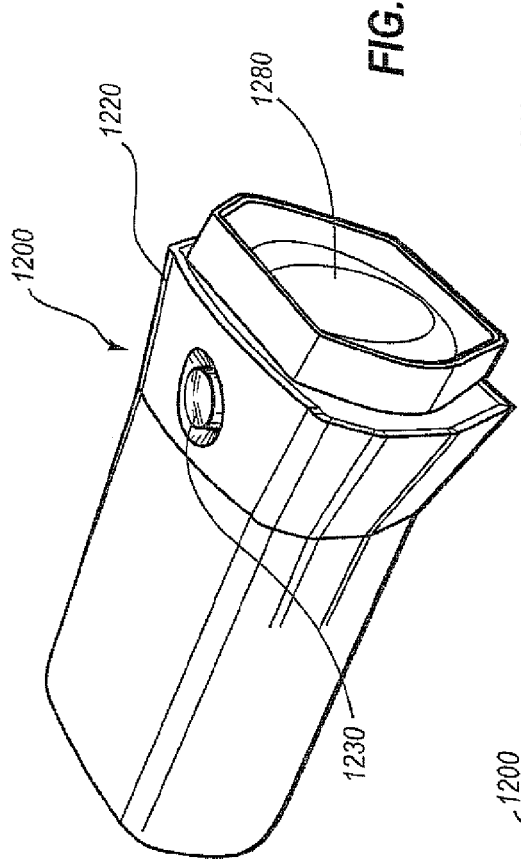
FIG. 40 is a perspective view of an exemplary light-emitting device according to certain embodiments.

FIG. 40 is a perspective view of an exemplary light-emitting device 1200. Light-emitting device 1200 may comprise a hand-held and/or a mounted lighting device, such as, for example, a head-lamp blood tracking device. As illustrated in this figure, light-emitting device 1200 may comprise a head 1220, a button 1230, and a refractive lens 1280.

Figure 41:
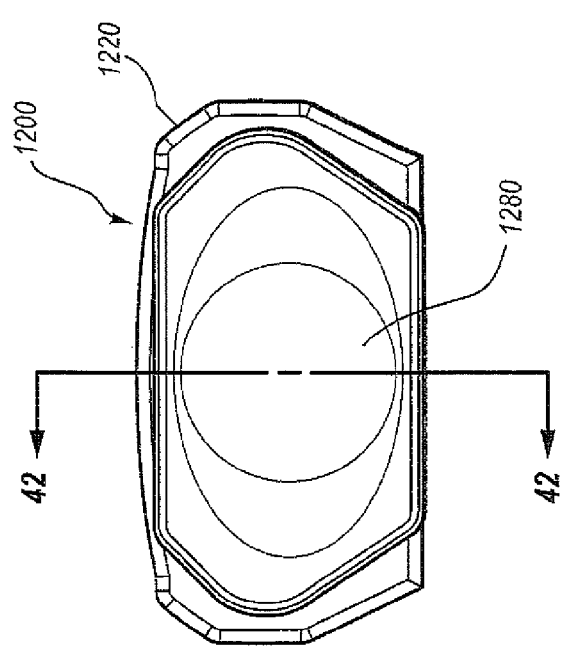
FIG. 41 is a front view of an exemplary light-emitting device according to certain embodiments.

FIG. 41 is a front view of light-emitting device 1200. As shown in this figure, light-emitting device 1200 may comprise a head 1220 and a refractive lens 1280. Refractive lens 1280 may comprise any type of refractive lens capable of transmitting and/or refracting light. For example, refractive lens 1280 may comprise one or more concave and/or convex surfaces for directing light, such as light from a light source.

Figure 42:
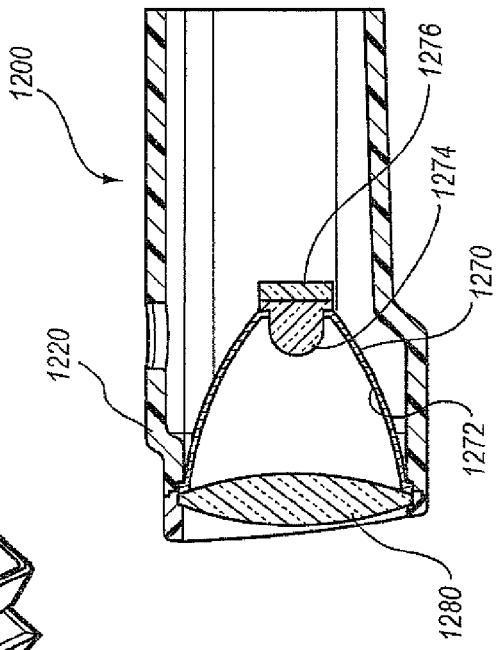
FIG. 42 is cross-sectional side view of an exemplary light-emitting device according to certain embodiments.

FIG. 42 is a cross-sectional side view of light-emitting device 1200 taken along line 42-42 in FIG. 41. As illustrated in this figure, light-emitting device 1200 may comprise a head 1220 and a refractive lens 1280. Additionally, light-emitting device 1200 may include a light source 1276, a refractive lens 1274, and a reflector 1270. Light source 1276 may comprise any suitable light source configured to emit both a red light and a light having a peak wavelength of approximately 565 nanometers or less, such as, for example, a green light. In various embodiments, light source 1276 may comprise two or more light sources configured to emit two or more colors of light. For example, light source 1276 may comprise a first light source configured to emit red light and a second light source configured to emit green light and/or visible light having a peak wavelength of approximately 565 nanometers or less.

In at least one embodiment, light source 1276 may comprise an LED having two or more separate light-emitting surfaces or chips placed in relatively close proximity to each other. For example, in at least one embodiment, two or more light-emitting surfaces may be spaced apart a distance of less than approximately 0.125 inches from center to center of the light-emitting surfaces. In additional embodiments, two or more light-emitting surfaces may be spaced apart a distance of between approximately 0.125 inches and approximately 0.060 inches. Light source 1276 may additionally be rated to any suitable wattage. For example, in at least one embodiment, light source 1276 may comprise an LED having two or more separate light-emitting surfaces or chips, each of which is rated to between approximately 1 watt and approximately 3 watts.

Refractive lens 1274 may be positioned in relatively close proximity to light source 1276, and may be positioned and configured to direct light emitted by light source 1276. Additionally, refractive lens 1274 may be positioned between light source 1276 and refractive lens 1280, as shown in FIG. 42. Refractive lens 1274 may comprise any type of refractive lens capable of transmitting and/or refracting light. For example, refractive lens 1274 may comprise one or more concave and/or convex surfaces for directing light, such as light from light source 1276. According to various embodiments, refractive lens 1274 may be configured to separate and/or direct light transmitted by light source 1276. Additionally, an optical axis of refractive lens 1274 may be substantially parallel to an optical axis of refractive lens 1280. In additional embodiments, refractive lens 1274 and refractive lens 1280 may share a common or substantially common optical axis.

Reflector 1270 may comprise a concave reflector surface 1272 configured to reflect light. Concave reflector surface 1272 may include a curved and/or reflective surface. Reflector 1270 may be positioned such that at least a portion of light emitted by light source 1276 may be reflected toward refractive lens 1280. Reflector 1270 may be disposed such that light emitted by light source 1276 passes through a first aperture in reflector 1270 and exits through a second aperture in reflector 1270. In various embodiments, refractive lens 1274 may be disposed in or near a first aperture in reflector 1270 and refractive lens 1280 may be disposed in or near a second aperture in reflector 1270, as shown in FIG. 42.

Figure 43:
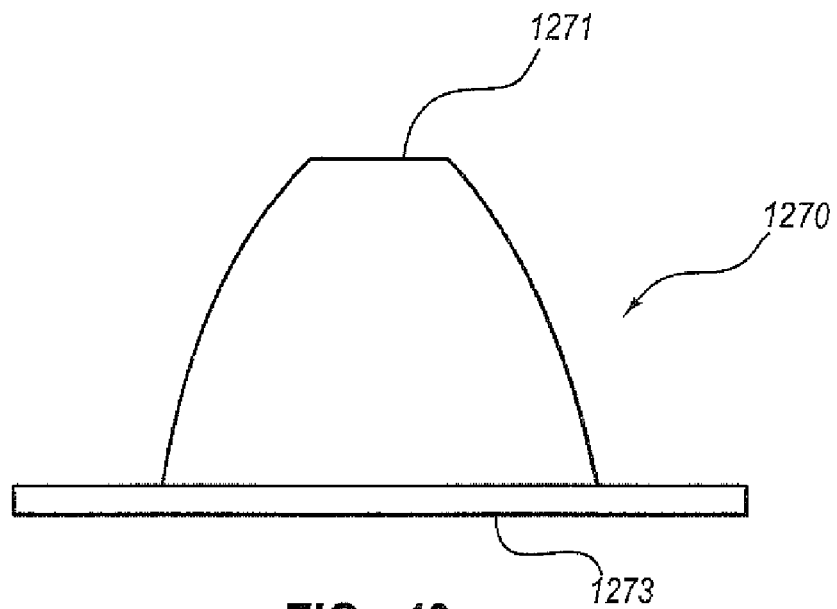
FIG. 43 is a top view of an exemplary reflector according to certain embodiments.
Figure 44:
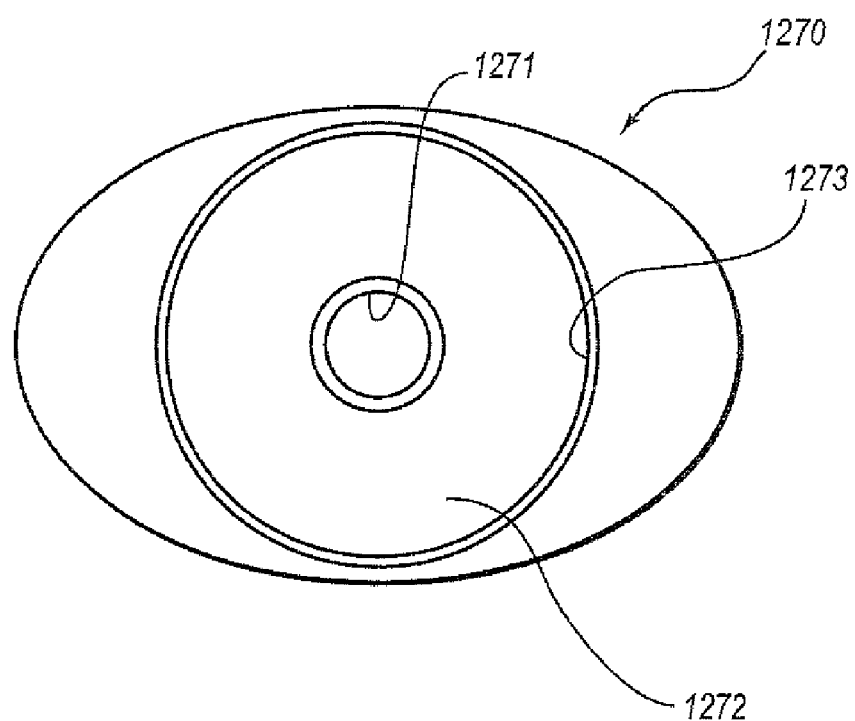
FIG. 44 is a front view of an exemplary reflector according to certain embodiments.

FIG. 43 is a top view of reflector 1270 and FIG. 44 is a front view of reflector 1270, according to various embodiments. As shown in these figures, reflector 1270 may comprise a concave reflector surface 1272, a first aperture 1271, and a second aperture 1273. First aperture 1271 may be sized to fit around light source 1276 and/or refractive lens 1274 (see, e.g., FIG. 42). Second aperture 1273 may be sized to fit around refractive lens 1280. Additionally, second aperture 1273 may be formed to a larger diameter than first aperture 1271, and concave reflector surface may be curved and/or sloped between first aperture 1271 and second aperture 1273.

Figure 45:
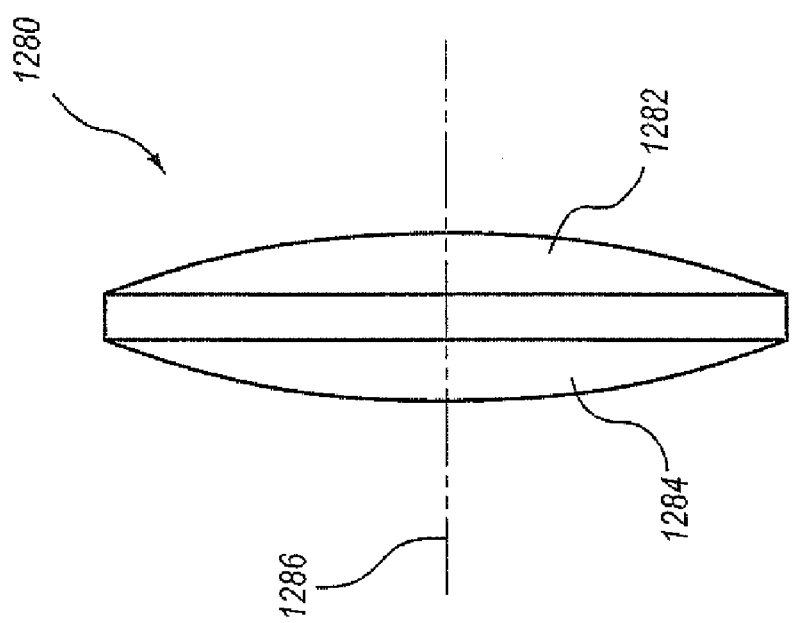
FIG. 45 is a side view of an exemplary lens according to certain embodiments.

FIG. 45 is a side view of an exemplary refractive lens 1280. As illustrated in this figure, refractive lens 1280 may have a first optical surface 1282 and a second optical surface 1284. Either or both of first optical surface 1282 and second optical surface 1284 may be concave and/or convex. First optical surface 1282 and/or second optical surface 1284 may be capable of bending light, thereby enabling refractive lens 1280 to transmit and/or refract light contacting and passing through refractive lens 1280. In various embodiments, refractive lens 1280 may have a diopter of between approximately 28 and approximately 40. Additionally, refractive lens 1280 may have a magnification power of between approximately 7 and approximately 10.

Refractive lens 1280 may have an optical axis 1286 passing through first optical surface 1282 and second optical surface 1284. In various embodiments, optical axis 1286 may pass through a central portion of refractive lens 1280. Light emitted by light source 1276 may coincide with refractive lens 1280 and/or may be directed toward refractive lens 1280 by refractive lens 1274 and/or reflector 1270. According to various embodiments, reflector 1270, refractive lens 1274, and/or light source 1276 may be substantially centered with respect to optical axis 1286.

Figure 46:
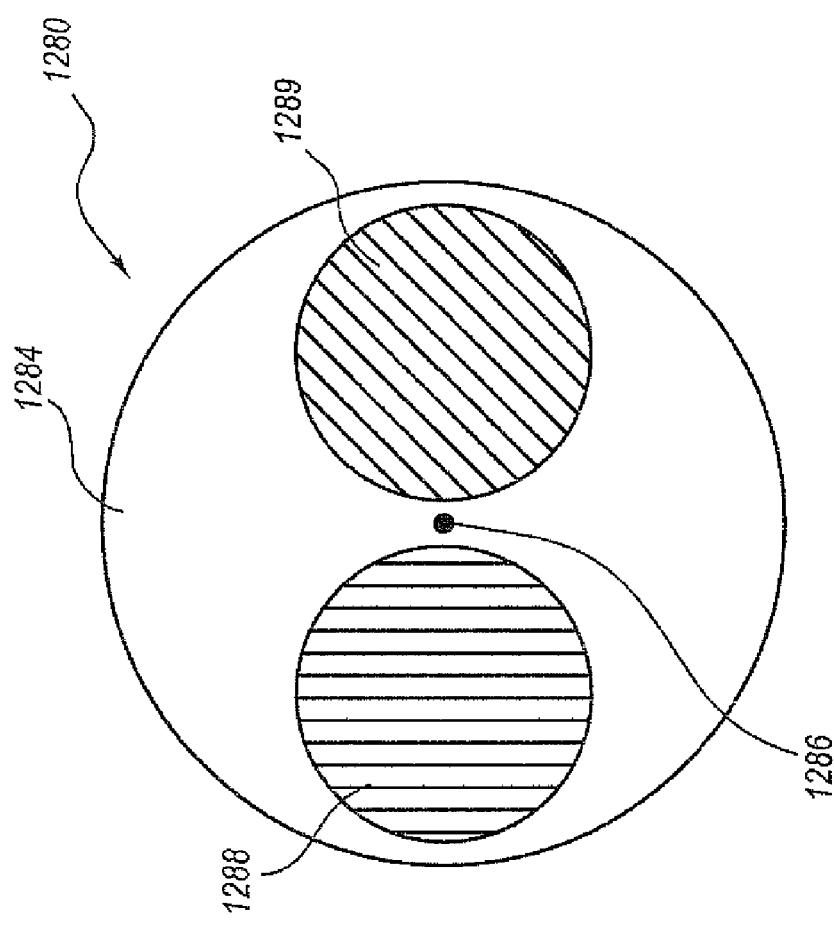
FIG. 46 is a front view of an exemplary lens according to certain embodiments.

FIG. 46 is a front view of an exemplary refractive lens 1280. This figure illustrates light exiting refractive lens 1280. Light emitted by light source 1276 may contact refractive lens 1280. For example, light emitted by light source 1276 may come in to contact with first optical surface 1282, passing through refractive lens 1280, and exiting through second optical surface 1284 as shown. In at least one example, light source 1276 may emit both red light and green light. Red light and the green light emitted by light source 1276 may be separated and/or directed by refractive lens 1274 prior to contacting refractive lens 1280. Additionally, at least a portion of the light emitted light source 1276 may contact and be reflected by reflector 1272. Light may be transferred from light source 1276, refractive lens 1274, and/or reflector 1272 to refractive lens 1280.

As shown in FIG. 46, light emitted by light source 1276 may be substantially or completely separated into two or more separate beams prior to entering and/or upon exiting refractive lens 1280. For example, as illustrated in FIG. 46, red light may exit second optical surface 1284, as represented by red light pattern 1288. Similarly, green light may exit second optical surface 1284, as represented by green light pattern 1289. In various embodiments, red light pattern 1288 and green light pattern 1289 on second optical surface 1284 may be substantially or completely separated. Additionally, as shown in FIG. 46, optical axis 1286 may be positioned between red light pattern 1288 and green light pattern 1289. In additional embodiments, optical axis may be located within red light pattern 1288 and/or green light pattern 1289. Red light pattern 1288 and green light pattern 1289 may be positioned at varying distances relative to each other and optical axis 1286. In at least one embodiment, red light pattern 1288 and green light pattern 1289 may be positioned approximately equidistant from optical axis 1286.

Figure 47:
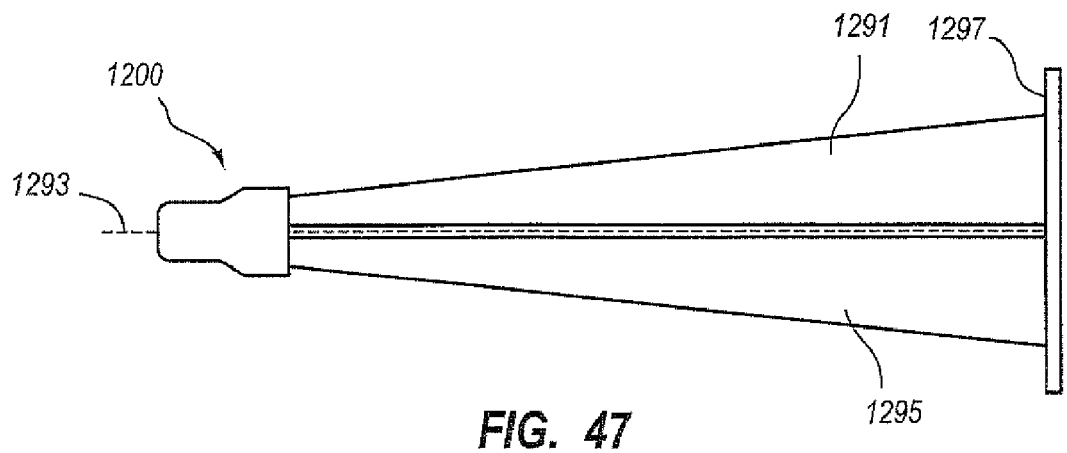
FIG. 47 is an illustration of a light-emitting device emitting light toward a target surface FIG. 48 an illustration of a pattern of green and red light according to certain embodiments.

FIG. 47 illustrates light-emitting device 1200 emitting light toward a target surface. As shown in this figure, light-emitting device 1200 may emit red light beam 1291 and green light beam 1295 toward a target surface 1297, which may include ground and/or other objects or surfaces. Red light beam 1291 may exit from refractive lens 1280 at or near red light pattern 1288 and green light beam 1295 may exit from refractive lens 1280 at or near green light pattern 1289 (see, e.g., FIG. 46). Upon exiting refractive lens 1280 of light-emitting device 1200, each of red light beam 1291 and green light beam 1295 may widen, narrow, or remain substantially the same width between refractive lens 1280 and target surface 1297. For example, as shown in FIG. 47, each of red light beam 1291 and green light beam 1295 may widen between light-emitting device 1200 and target surface 1297.

Red light beam 1291 may exit from refractive lens 1280 at or near red light pattern 1288 and green light beam 1295 may exit from refractive lens 1280 at or near green light pattern 1289, and as described above, optical axis 1286 of refractive lens 1280 may be positioned between red light pattern 1288 and green light pattern 1289 (see, e.g., FIG. 46). In at least one embodiment, an outer longitudinal portion of red light beam 1291 and an outer longitudinal portion of the green light beam 1295 may be substantially parallel to optical axis 1286 of refractive lens 1280 and/or may be substantially parallel to a projection axis 1293, as illustrated in FIG. 47. Projection axis 1293 may represent an axis and/or line between red light beam 1291 and green light beam 1295. In various embodiments, projection axis 1293 may be parallel to optical axis 1286. In additional embodiments, projection axis 1293 may be formed at an angle to optical axis 1286.

In certain embodiments, red light beam 1291 and green light beam 1295 may be in close proximity to each other. In additional embodiments, red light beam 1291 and green light beam 1295 may at least partially overlap. An interface may be present between red light beam 1291 and green light beam 1295 at an area where red light beam 1291 and green light beam 1295 are in close proximity to each other. In addition, an interface may be present between red light beam 1291 and green light beam 1295 at an area where red light beam 1291 and green light beam 1295 overlap each other. According to certain embodiments, red light beam 1291 and green light beam 1295 are substantially parallel in a longitudinal direction at and/or near an interface between red light beam 1291 and green light beam 1295.

By maintaining red light beam 1291 and green light beam 1295 in a substantially parallel configuration with respect to an interface and/or projection axis 1293 between red light beam 1291 and the green light beam 1295, red light beam 1291 and/or green light beam 1295 may be capable of illuminating an area without creating distracting red and/or green light patterns, shadow patterns, and/or other visual artifacts when an object intercepts red light beam 1291 and/or green light beam 1295. Light-emitting device 1200 may additionally be capable of illuminating an area without creating distracting red and/or green light patterns, shadow patterns, and/or other visual artifacts when an object intercepts red light beam 1291 and/or green light beam 1295 by maintaining light red light beam 1291 and green light beam 1295 in a substantially non-overlapping configuration.

For example, when light-emitting device 1200 is used to illuminate an area that has a branch between light-emitting device 1200 and target surface 1297, green light beam 1295 may coincide with the branch, causing a shadow in the green light on target surface 1297. Because red light, beam 1291 does not substantially intersect a portion of green light beam 1295 coinciding with the branch and/or because red light beam 1291 is substantially parallel to a portion of green light beam 1295, a portion of red light beam 1291 may not substantially coincide with the shadow in the green light on target surface 1297. Accordingly, the shadow in the green light on target surface 1297 may not contain an amount of red light capable of causing an unusual and/or confusing pattern of light visible by a hunter using light-emitting device 1200.

Additionally, by maintaining red light beam 1291 and green light beam 1295 in a substantially parallel configuration with respect to an interface and/or projection axis 1293 between red light beam 1291 and green light beam 1295, red light beam 1291 and/or green light beam 1295 may be capable of effectively illuminating a target surface 1297 located at varying distances from light-emitting device 1200. For example, red light beam 1291 and green light beam 1295 may be in close proximity to each other at varying distances from light-emitting device 1200.

Figure 48:
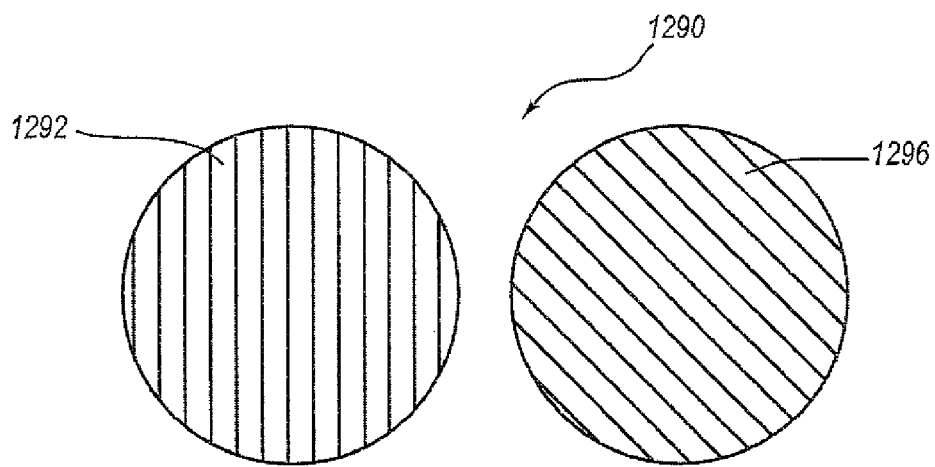
Figure 49:
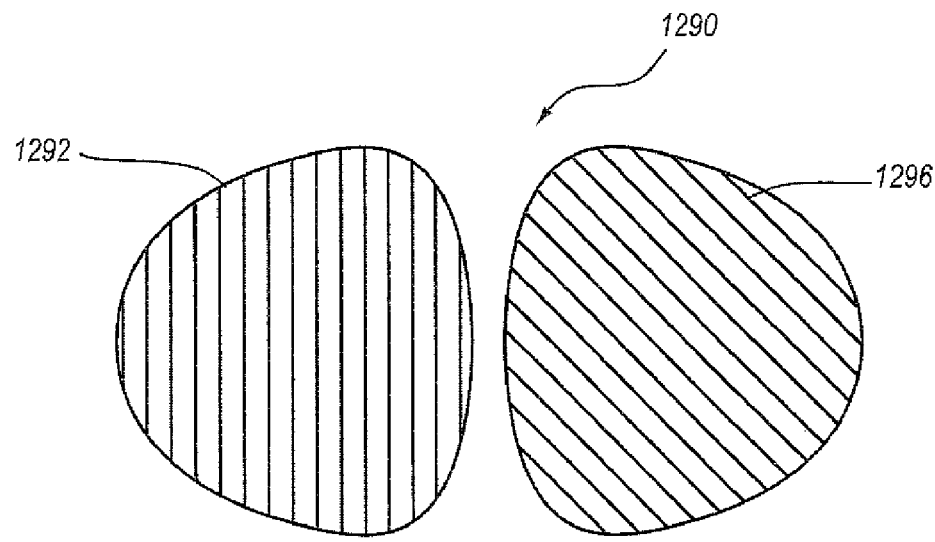
FIG. 49 an illustration of a pattern of green and red light according to certain embodiments.

FIGS. 48 and 49 illustrate representative surface patterns of light that may be emitted by light-emitting device 1200. Surface pattern 1290 may represent a cross-section of light emitted by light-emitting device 1200 and/or may represent a pattern of light at an area where light emitted by light-emitting device 1200 coincides with a target surface 1297 (see, e.g., FIG. 47). Red light pattern 1292 of surface pattern 1290 may comprise red light and green light pattern 1296 of surface pattern 1290 may comprise green light and/or light having a wavelength of approximately 565 nanometers or less. Red light pattern 1292 may represent a pattern formed by red light beam 1291 and green light pattern 1296 may represent a pattern formed by green light beam 1295. As shown in these figures, red light pattern 1292 and green light pattern 1296 may be in close proximity. In additional embodiments, red light pattern 1292 and/or green light pattern 1296 may at least partially overlap.

Figure 50:
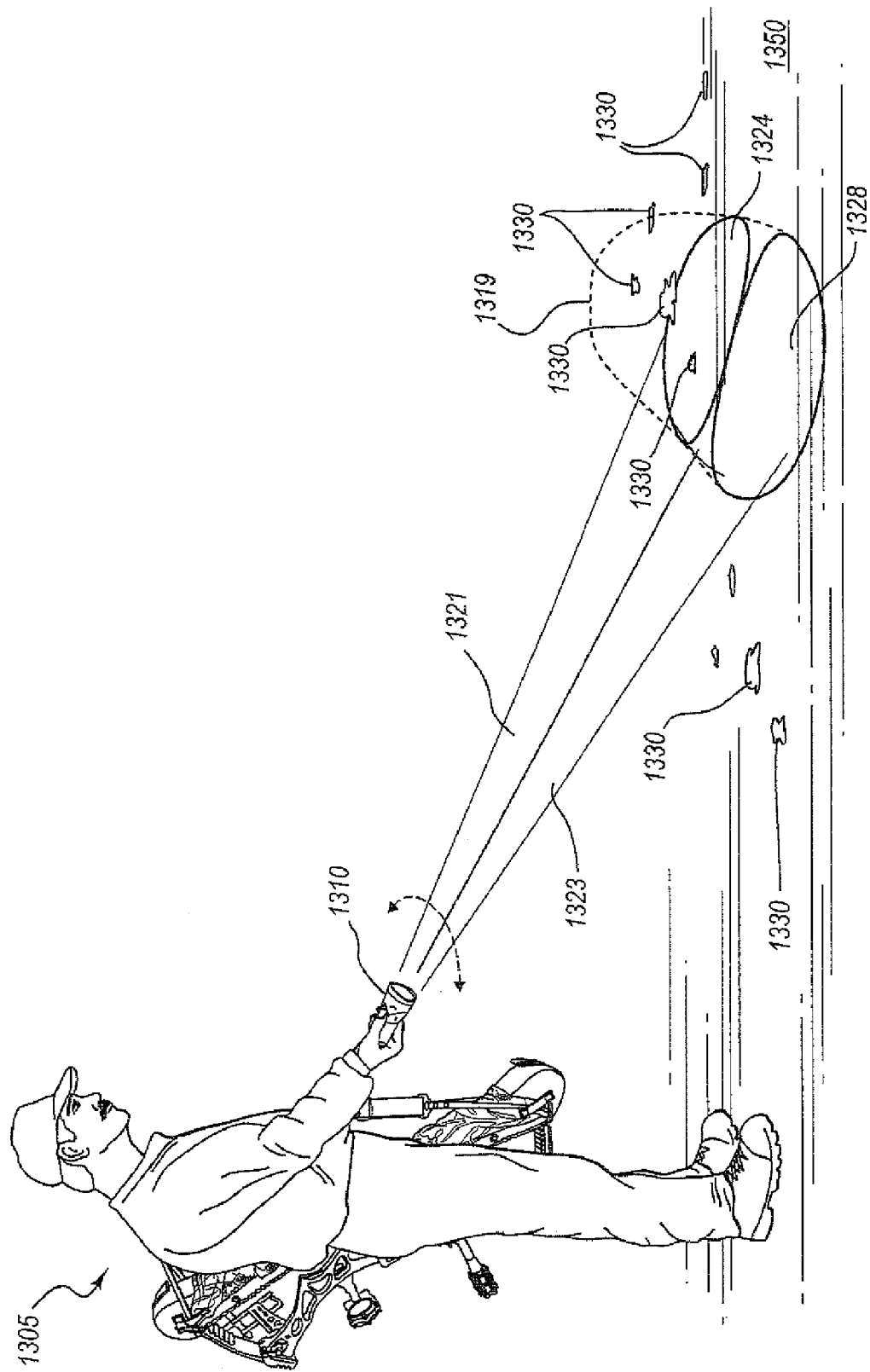
FIG. 50 is a scene illustrating an exemplary use of a light-emitting device according to certain embodiments.

FIG. 50 is a scene of a hunter using a light-emitting device 1300. Light-emitting device 1300 may illuminate a lighted region 1320 on ground 1350. Lighted region 1320 may include a red light region 1324 and a green light region 1328. Hunter 1305 may be tracking a trail of blood 1330 left by wounded game (not shown). Hunter 1305 may scan ground 1350 looking for a trail of blood 1330. Scanning the ground with light-emitting device 1300 may cause blood 1330 to appear to blink and/or otherwise stand out in contrast to nearby portions of ground 1350, thereby helping blood 1330 stand out to hunter 1305 in contrast to leaves, twigs, dirt, or other objects.

According to at least one embodiment, hunter 1305 may scan ground 1350 with light-emitting device 1300 such that light region 1320 generally follows a side-to-to side path or sweeping path 1319, as illustrated in FIG. 50. Light-emitting device 1300 may be held in such a manner that blood 1330 is intermittently lighted by red light region 1324 and green light region 1328. As red light region 1324 and green light region 1328 intermittently light blood 1330, the contrasting red light and green light may cause blood 1330 to stand out visually in contrast to ground 1350.

For example, green light region 1328 may contain green light and/or light having a peak wavelength of approximately 565 nanometers or less. The green light region 1328 may strike blood 1330 and may make blood 1330 appear a dark color. When red light in red light region 1324 strikes blood 1330, the red light may make blood 1330 appear a highly red color, particularly in relation to the surroundings on and around ground 1350. The alternating lighting of blood 1330 by green light region 1328 and red light region 1324 may cause the eye to perceive the red color as being particularly bright and noticeable in comparison to the surroundings. Additionally, the alternating lighting of blood 1330 by green light region 1328 and red light region 1324 may cause the eye to perceive that blood 1330 is blinking as the color of light striking blood 1330 alternates between red light and green light. This apparent blinking may trigger the motion circuitry in the brain and/or may otherwise help blood-red colors visually stand out in contrast to other colors.

Additionally, by maintaining red light beam 1321 and green light beam 1323 in a substantially parallel configuration with respect to an interface and/or projection axis between red light beam 1321 and green light beam 1323 (see, e.g., FIG. 47), red light beam 1321 and/or green light beam 1323 may be able to effectively illuminate blood located at varying distances from light-emitting device 1300. For example, red light beam 1321 and green light beam 1323 may be in close proximity to each other at varying distances from light-emitting device 1300.

Figure 51:
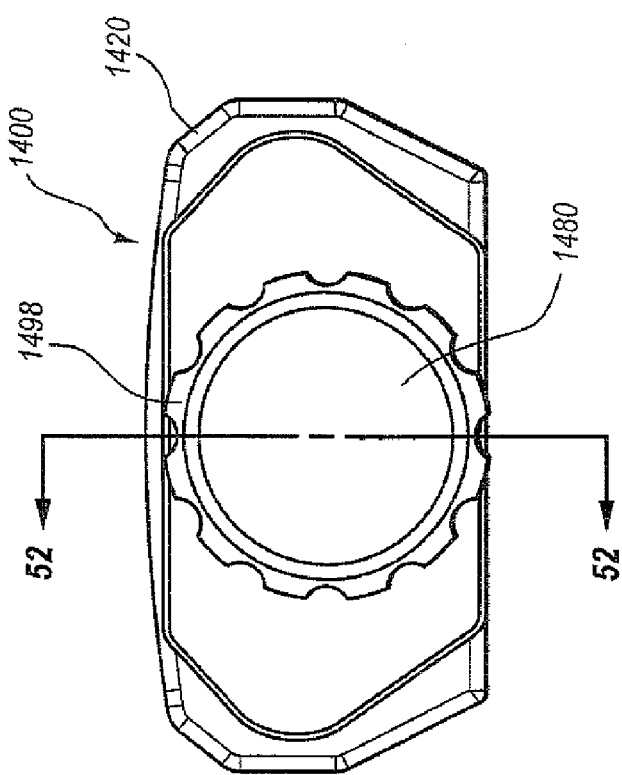
FIG. 51 is a front view of an exemplary light-emitting device according to certain embodiments.

FIG. 51 is a front view of light-emitting device 1400. As shown in this figure, light-emitting device 1400 may comprise a head 1420 and a refractive lens 1480. Refractive lens 1480 may comprise any type of refractive lens capable of transmitting and/or refracting light. For example, refractive lens 1480 may comprise one or more concave and/or convex surfaces for directing light, such as light from a light source.

Figure 52:
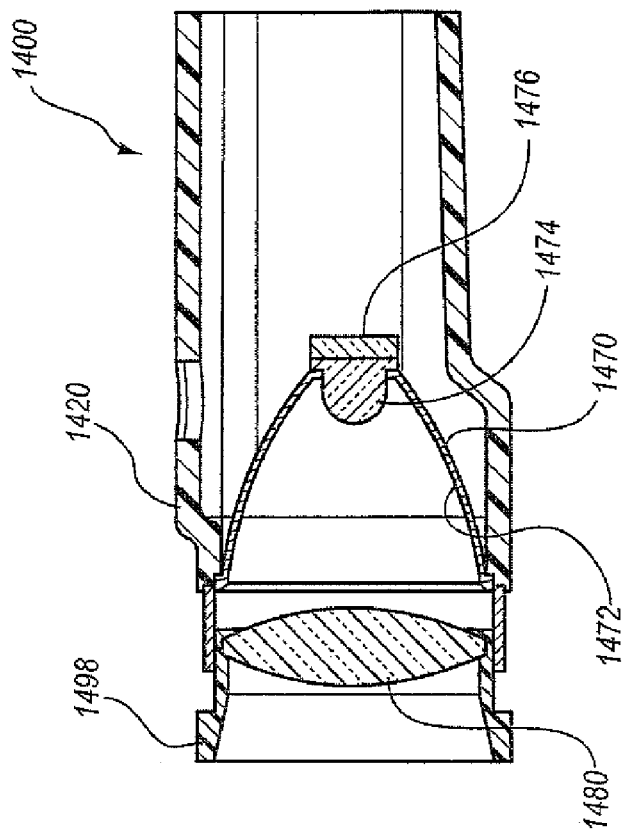
FIG. 52 is cross-sectional side view of an exemplary light-emitting device according to certain embodiments.

FIG. 52 is a cross-sectional side view of light-emitting device 1400 taken along line 52-52 in FIG. 51. As illustrated in this figure, light-emitting device 1400 may comprise a head 1420 and a refractive lens 1480. Additionally, light-emitting device 1400 may include a light source 1476, a refractive lens 1474, and a reflector 1470. In various embodiments, light source 1476 may comprise two or more light sources configured to emit two or more colors of light. For example, light source 1476 may comprise a first light source configured to emit red light and a second light source configured to emit green light and/or visible light having a peak wavelength of approximately 565 nanometers or less.

An optical axis of refractive lens 1474 may be substantially parallel to an optical axis of refractive lens 1480. In additional embodiments, refractive lens 1474 and refractive lens 1480 may substantially share a common optical axis. Reflector 1470 may comprise a concave reflector surface 1472. Additionally, light-emitting device 1400 may comprise an optical adjuster 1498. Optical adjuster 1498 may be configured to adjust a separation distance between refractive lens 1480 and light source 1476. In additional embodiments, optical adjuster 1498 may be configured to adjust a separation distance between refractive lens 1480 and refractive lens 1474.

Optical adjuster 1498 may comprise any adjuster suitable for moving refractive lens 1480, light source 1476, and/or refractive lens 1474. According to various embodiments, optical adjuster 1498 may be configured to hold refractive lens 1480, as shown in FIG. 52. Optical adjuster 1498 may additionally be configured to move refractive lens 1480 further away from or closer to light source 1476 and/or refractive lens 1474 when optical adjuster 1498 is rotated with respect to light-emitting device 1400. In additional embodiments, optical adjuster 1498 may be configured to rotate with respect to light-emitting device 1400. According to certain embodiments, a portion of optical adjuster 1498 may be rotatable about an optical axis of refractive lens 1480. Optical adjuster 1498 may also be configured to remain a substantially constant distance from light source 1476 and/or refractive lens 1474 when optical adjuster 1498 is rotated, while at the same time moving refractive lens 1480 further away from or closer to light source 1476 and/or refractive lens 1474. Additionally, optical adjuster 1498 may be configured to move refractive lens 1480 in a direction substantially parallel to an optical axis of refractive lens 1480.

By moving refractive lens 1480 further away from or closer to light source 1476 and/or refractive lens 1474, optical adjuster 1498 may enable a user of light-emitting device 1400 to focus, spread, and/or widen light beams emitted by light-emitting device 1400 (see, e.g., red light beam 1291 and green light beam 1295 in FIG. 47). In additional embodiments, by moving refractive lens 1480 further away from or closer to light source 1476 and/or refractive lens 1474, optical adjuster 1498 may enable a user of light-emitting device 1400 to bring closer and/or separate light beams emitted by light-emitting device 1400.

Figure 53:
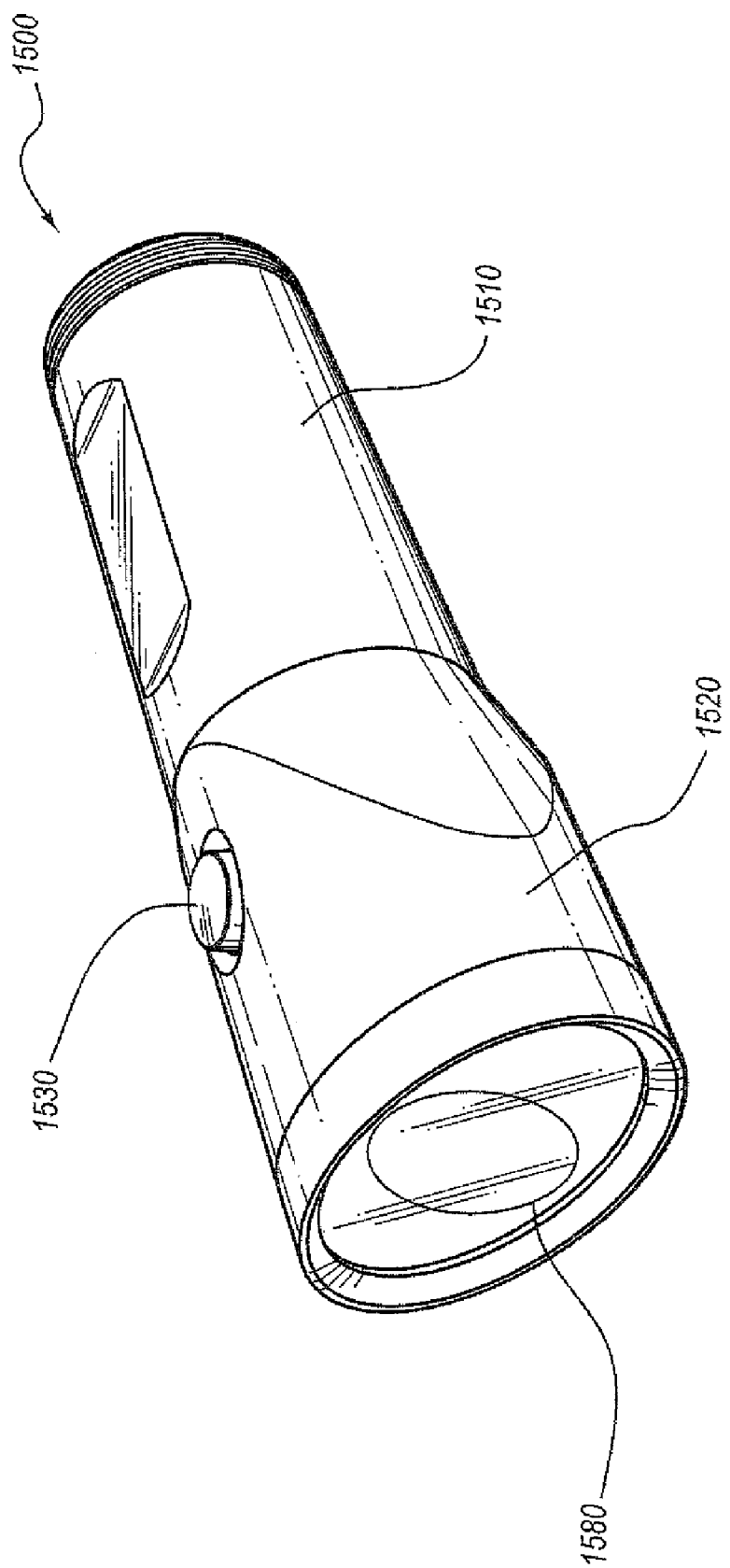
FIG. 53 is a perspective view of an exemplary light-emitting device according to certain embodiments.

FIG. 53 is a perspective view of an exemplary light-emitting device 1500. Light-emitting device 1500 may comprise a hand-held lighting device. As illustrated in this figure, light-emitting device 1500 may comprise a handle 1510, a head 1520, a button 1530, and a refractive lens 1580. Additionally, light-emitting device 1500 may include a light source (see, e.g., light source 1276 in FIG. 42).

Figure 54:
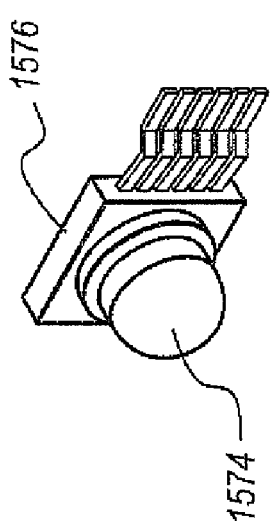
FIG. 54 is a perspective view of an exemplary light source and refractive lens according to certain embodiments.

FIG. 54 illustrates a light source 1576 and a refractive lens 1574. As illustrated in this figure, refractive lens 1574 may cover at least a portion of light source 1576. Refractive lens 1574 may additionally be positioned in relatively close proximity to light source 1576, and may be positioned and configured to direct light emitted by light source 1576. Light emitted by light source 1576 may be separated and/or directed by refractive lens 1574.

Figure 55:
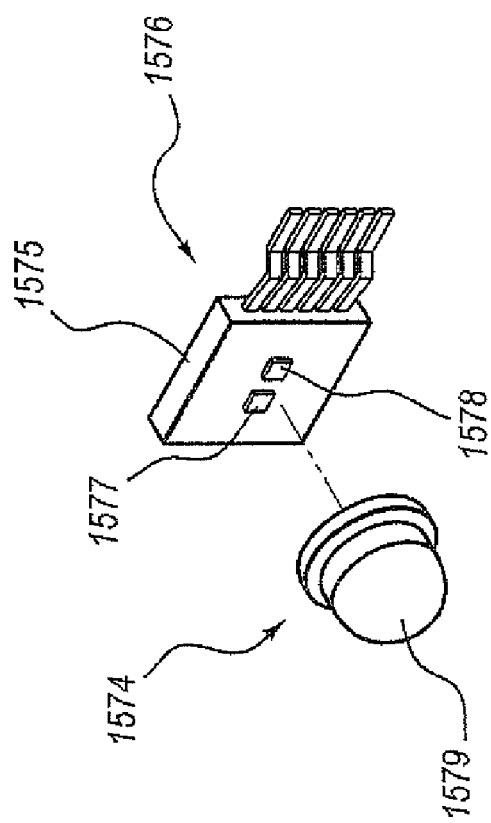
FIG. 55 is a perspective view of an exemplary light source and refractive lens according to certain embodiments.

FIG. 55 illustrates a light source 1576 and a refractive lens 1574. As illustrated in this figure, refractive lens 1574 may comprise an optical surface 1579 for refracting and/or directing light emitted by light source 1576. In various embodiments, refractive lens 1574 may comprise at least an additional refractive surface on an interior surface defined in refractive lens 1574.

In various embodiments, light source 1576 may comprise two or more light sources configured to emit two or more colors of light. For example, light source 1576 may comprise a first light source configured to emit red light and a second light source configured to emit green light and/or visible light having a peak wavelength of approximately 565 nanometers or less. For example, as shown in FIG. 55, light source 1576 may comprise an LED surface 1575 on which green light emitting surface 1577 and red light emitting surface 1578 may be layered. In at least one embodiment, light source 1576 may comprise an LED having two or more separate light-emitting surfaces or chips placed in relatively close proximity to each other on LED surface 1575.

Green light emitting surface 1577 may emit green light and/or light having a peak wavelength of approximately 565 nanometers or less. Red light emitting surface 1578 may emit red light. According to at least one embodiment, red light emitting surface 1578 may emit red light having a peak wavelength between approximately 610 nanometers and approximately 680 nanometers. In certain embodiments, red light emitting surface 1578 may emit red light having a peak wavelength between approximately 636 nanometers and 644 nanometers. Green light emitting surface 1577 and red light emitting surface 1578 may comprise portions of one or more light emitting diodes.

In various embodiments, green light emitting surface 1577 may be spaced apart from red light emitting surface 1578 a distance of approximately 0.125 inches or less from center to center of the light-emitting surfaces. In additional embodiments, green light emitting surface 1577 may be spaced apart from red light emitting surface 1578 a distance of between approximately 0.125 inches and approximately 0.060 inches from center to center of the light-emitting surfaces. Light source 1576 and/or diodes comprising green light emitting surface 1577 and red light emitting surface 1578 may additionally be rated to any suitable wattage. For example, in at least one embodiment, light source 1576 and/or diodes comprising green light-emitting surface 1577 and red light-emitting surface 1578 may each be rated to between approximately 1 watt and approximately 3 watts. According to various embodiments, red light-emitting surface 1578 may be a red light source and green light-emitting surface 1577 may be a green light source.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive, and that reference be made to the appended claims and their equivalents for determining the scope of the instant disclosure. In addition, for ease of use, the words "including" and "having," as used in the specification and claims, are interchangeable with and have the same meaning as the word "comprising."

What is claimed is:

1. An apparatus comprising:
a light-emitting device configured to illuminate a trail of blood from a wounded game animal, the light-emitting device comprising:
a red light source configured to emit red light;
a green light source configured to emit green light;
a first refractive lens configured to direct red light emitted by the red light source to form a red light beam and to direct green light emitted by the green light source to form a green light beam, wherein the red light beam and the green light beam provide a zone of overlapping red and green light outside of the device, the zone of overlapping red and green light when projected onto the blood causing the blood to stand out when following the trail of blood from the wounded game animal; and
an optical adjuster configured to adjust a separation distance between the first refractive lens and at least one of the red light source and the green light source.

2. The apparatus of claim 1, wherein the optical adjuster is configured to move the first refractive lens with respect to at least one of the red light source and the green light source.

3. The apparatus of claim 2, wherein the optical adjuster is configured to move the first refractive lens in a direction parallel to an optical axis of the first refractive lens.

4. The apparatus of claim 1, wherein the optical adjuster is configured to adjust a width of at least one of the red light beam and the green light beam.

5. The apparatus of claim 1, wherein the optical adjuster is configured to adjust a proximity of the red light beam to the green light beam.

6. The apparatus of claim 1, wherein a portion of the optical adjuster is rotatable about an optical axis of the first refractive lens.

7. The apparatus of claim 1, further comprising a reflector configured to reflect a portion of red light emitted by the red light source and a portion of green light emitted by the green light source toward the first refractive lens.

8. The apparatus of claim 1, further comprising a second lens having an optical axis parallel to an optical axis of the first refractive lens.

9. The apparatus of claim 1, wherein at least one of the red light source and the green light source comprises a light-emitting surface of a light-emitting diode.

10. The apparatus of claim 1, wherein red light emitted by the red light source has a peak wavelength between 610 nanometers and 680 nanometers.

11. The apparatus of claim 1, wherein the center of a light emitting surface of the red light source and the center of a light emitting surface of the green light source are spaced apart a distance of less than 0.125 inches.

12. The apparatus of claim 1, wherein the first refractive lens has a diopter of between 28 and 40.

13. The apparatus of claim 1, wherein the first refractive lens has a magnification power of between 7 and 10.

14. The apparatus of claim 1, wherein the first refractive lens has an optical axis, the first refractive lens being configured to emit a majority of the red light beam and a majority of the green light beam from surface portions of the first refractive lens on radially opposite sides of the optical axis.

15. An apparatus comprising: a light-emitting device configured to illuminate a trail of blood from a wounded game animal, the light-emitting device comprising: a red light source configured to emit a first light beam comprising red light; a green light source configured to emit a second light beam comprising green light; wherein the first light beam and the second light provide a zone of overlapping first and second light beams outside of the device, the zone of overlapping first and second light beams when projected onto blood causing the blood to stand out when following the trail of blood from the wounded game animal, the light-emitting device further comprising a divider positioned between the first and second light sources and operable to maintain separation of the first light beam and the second light beam within the device.

16. A method of illuminating blood, comprising:
providing a light-emitting device configured to illuminate a trail of blood from a wounded game animal, the light-emitting device comprising:
a red light source configured to emit red light;
a green light source configured to emit visible light having a peak wavelength of between 500 and 565 nanometers;

a refractive lens configured to direct red light emitted by the first light source to form a first light beam and to direct visible light emitted by the second light source to form a second light beam;

emitting red light from the first light source and visible light from the second light source to form the first light beam and the second light beam;

moving the light-emitting device such that a portion of the first light beam, a portion of the second light beam, and a zone of overlapping first and second light beams alternately illuminate the trail of blood from the wounded animal, to cause the blood to stand out and allow a hunter to follow the blood trail of the wounded game animal.

17. The method of claim 16, further comprising adjusting a separation distance between the refractive lens and at least one of the red light source and the green light source.

18. The method of claim 16, wherein:

red light emitted by the red light source has a peak wavelength between 610 nanometers and 680 nanometers;

visible light emitted by the green light source has a peak wavelength between 500 nanometers and 540 nanometers.

19. The method of claim 16, wherein the light-emitting device further comprises a reflector having a concave surface to reflect a portion of red light emitted by the red light source and a portion of visible light emitted by the green light source toward the refractive lens.

* * * * *